United States Patent
Heruth et al.

(10) Patent No.: US 9,623,248 B2
(45) Date of Patent: *Apr. 18, 2017

(54) COLLECTING SLEEP QUALITY INFORMATION VIA A MEDICAL DEVICE

(71) Applicant: Medtronic, Inc., Minneapolis, MN (US)

(72) Inventors: Kenneth T. Heruth, Edina, MN (US); Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/961,344

(22) Filed: Dec. 7, 2015

(65) Prior Publication Data

US 2016/0158552 A1 Jun. 9, 2016

Related U.S. Application Data

(60) Continuation of application No. 14/276,516, filed on May 13, 2014, now Pat. No. 9,205,264, which is a
(Continued)

(51) Int. Cl.
*A61B 5/00* (2006.01)
*A61B 5/04* (2006.01)
(Continued)

(52) U.S. Cl.
CPC .......... *A61N 1/36139* (2013.01); *A61B 3/113* (2013.01); *A61B 5/01* (2013.01);
(Continued)

(58) Field of Classification Search
None
See application file for complete search history.

(56) References Cited

U.S. PATENT DOCUMENTS

| 4,297,685 A | 10/1981 | Brainard, II |
| 4,550,736 A | 11/1985 | Broughton et al. |

(Continued)

FOREIGN PATENT DOCUMENTS

| DE | 19831109 A1 | 1/2000 |
| DE | 10024103 A1 | 11/2001 |

(Continued)

OTHER PUBLICATIONS

"Analysis of heart rate dynamics by methods derived from nonlinear mathematics: Clinical applicability and prognostic significance," http://herkules.oulu.fi.isbn9514250133/html, Oct. 2004, 4 pp.

(Continued)

*Primary Examiner* — Etsub Berhanu
(74) *Attorney, Agent, or Firm* — Carol F. Barry

(57) ABSTRACT

At least one of a medical device, such as an implantable medical device, and a programming device determines values for one or more metrics that indicate the quality of a patient's sleep. Sleep efficiency, sleep latency, and time spent in deeper sleep states are example sleep quality metrics for which values may be determined. In some embodiments, determined sleep quality metric values are associated with a current therapy parameter set. In some embodiments, a programming device presents sleep quality information to a user based on determined sleep quality metric values. A clinician, for example, may use the sleep quality information presented by the programming device to evaluate the effectiveness of therapy delivered to the patient by the medical device, to adjust the therapy delivered by the medical device, or to prescribe a therapy not delivered by the medical device in order to improve the quality of the patient's sleep.

29 Claims, 11 Drawing Sheets

Related U.S. Application Data continuation of application No. 12/723,501, filed on Mar. 12, 2010, now Pat. No. 8,758,242, which is a division of application No. 10/826,925, filed on Apr. 15, 2004, now Pat. No. 7,717,848.

(60) Provisional application No. 60/553,783, filed on Mar. 16, 2004.

(51) Int. Cl.

| | |
|---|---|
| A61N 1/36 | (2006.01) |
| A61B 5/0476 | (2006.01) |
| A61B 5/11 | (2006.01) |
| A61M 5/142 | (2006.01) |
| A61M 5/172 | (2006.01) |
| A61N 1/372 | (2006.01) |
| A61B 3/113 | (2006.01) |
| A61B 5/01 | (2006.01) |
| A61B 5/0402 | (2006.01) |
| A61N 1/37 | (2006.01) |
| A61N 1/365 | (2006.01) |

(52) U.S. Cl.
CPC .......... *A61B 5/0402* (2013.01); *A61B 5/0476* (2013.01); *A61B 5/1116* (2013.01); *A61B 5/1118* (2013.01); *A61B 5/4815* (2013.01); *A61B 5/686* (2013.01); *A61M 5/14276* (2013.01); *A61M 5/1723* (2013.01); *A61N 1/36071* (2013.01); *A61N 1/36078* (2013.01); *A61N 1/36135* (2013.01); *A61N 1/36514* (2013.01); *A61N 1/3702* (2013.01); *A61N 1/37247* (2013.01); *A61B 5/6826* (2013.01); *A61N 1/36521* (2013.01); *A61N 1/36542* (2013.01); *A61N 1/36557* (2013.01)

(56) References Cited

U.S. PATENT DOCUMENTS

| | | |
|---|---|---|
| 4,771,780 A | 9/1988 | Sholder |
| 4,776,345 A | 10/1988 | Cohen et al. |
| 4,846,195 A | 7/1989 | Alt |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,233,984 A | 8/1993 | Thompson |
| 5,275,159 A | 1/1994 | Griebel |
| 5,335,657 A | 8/1994 | Terry, Jr. et al. |
| 5,337,758 A | 8/1994 | Moore et al. |
| 5,342,409 A | 8/1994 | Mullett |
| 5,469,861 A | 11/1995 | Piscopo et al. |
| 5,476,483 A | 12/1995 | Bornzin et al. |
| 5,509,927 A | 4/1996 | Epstein et al. |
| 5,514,162 A | 5/1996 | Bornzin et al. |
| 5,591,216 A | 1/1997 | Testerman et al. |
| 5,593,431 A | 1/1997 | Sheldon |
| 5,622,428 A | 4/1997 | Bonnet |
| 5,645,053 A | 7/1997 | Remmers et al. |
| 5,683,432 A | 11/1997 | Goedeke et al. |
| 5,713,923 A | 2/1998 | Ward et al. |
| 5,732,696 A | 3/1998 | Rapoport et al. |
| 5,782,884 A | 7/1998 | Stotts et al. |
| 5,814,093 A | 9/1998 | Stein |
| 5,833,709 A | 11/1998 | Rise et al. |
| 5,851,193 A | 12/1998 | Arikka et al. |
| 5,895,371 A | 4/1999 | Levitas et al. |
| 5,904,708 A | 5/1999 | Goedeke |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,999,846 A | 12/1999 | Pardey et al. |
| 6,044,297 A | 3/2000 | Sheldon et al. |
| 6,045,513 A | 4/2000 | Stone et al. |
| 6,059,576 A | 5/2000 | Brann |
| 6,091,973 A | 7/2000 | Colla et al. |
| 6,094,598 A | 7/2000 | Elsberry et al. |
| 6,095,991 A | 8/2000 | Krausman et al. |
| 6,102,874 A | 8/2000 | Stone et al. |
| 6,120,467 A | 9/2000 | Schallhorn |
| 6,128,534 A | 10/2000 | Park et al. |
| 6,157,857 A | 12/2000 | Dimpfel |
| 6,161,095 A | 12/2000 | Brown |
| 6,165,143 A | 12/2000 | Van Lummel |
| 6,227,203 B1 | 5/2001 | Rise et al. |
| 6,259,948 B1 | 7/2001 | Florio et al. |
| 6,273,856 B1 | 8/2001 | Sun et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,315,740 B1 | 11/2001 | Singh |
| 6,351,672 B1 | 2/2002 | Park et al. |
| 6,366,813 B1 | 4/2002 | DiLorenzo |
| 6,416,471 B1 | 7/2002 | Kumar et al. |
| 6,433,690 B2 | 8/2002 | Petelenz et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,234 B1 | 10/2002 | Pyle et al. |
| 6,466,821 B1 | 10/2002 | Pianca et al. |
| 6,468,234 B1 | 10/2002 | Van der Loos et al. |
| 6,514,218 B2 | 2/2003 | Yamamoto |
| 6,539,249 B1 | 3/2003 | Kadhiresan et al. |
| 6,574,507 B1 | 6/2003 | Bonnet |
| 6,597,954 B1 | 7/2003 | Pless et al. |
| 6,605,038 B1 | 8/2003 | Teller et al. |
| 6,611,783 B2 | 8/2003 | Kelly, Jr. et al. |
| 6,626,902 B1 | 9/2003 | Kucharczyk et al. |
| 6,659,968 B1 | 12/2003 | McClure |
| 6,665,558 B2 | 12/2003 | Kalgren et al. |
| 6,687,538 B1 | 2/2004 | Hrdlicka et al. |
| 6,731,984 B2 | 5/2004 | Cho et al. |
| 6,735,474 B1 | 5/2004 | Loeb et al. |
| 6,752,766 B2 | 6/2004 | Kowallik et al. |
| 6,773,404 B2 | 8/2004 | Poezevera et al. |
| 6,819,956 B2 | 11/2004 | DiLorenzo |
| 6,878,121 B2 | 4/2005 | Krausman et al. |
| 6,881,192 B1 | 4/2005 | Park |
| 6,884,596 B2 | 4/2005 | Civelli et al. |
| 6,890,306 B2 | 5/2005 | Poezevera |
| 6,928,324 B2 | 8/2005 | Park et al. |
| 6,937,891 B2 | 8/2005 | Leinders et al. |
| 6,964,641 B2 | 11/2005 | Cho et al. |
| 7,130,689 B1 | 10/2006 | Turcott |
| 7,141,034 B2 | 11/2006 | Eppstein et al. |
| 7,151,961 B1 | 12/2006 | Whitehurst et al. |
| 7,155,279 B2 | 12/2006 | Whitehurst et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,209,787 B2 | 4/2007 | DiLorenzo |
| 7,309,314 B2 | 12/2007 | Grant et al. |
| 7,313,440 B2 | 12/2007 | Miesel |
| 7,330,760 B2 | 2/2008 | Heruth et al. |
| 7,366,572 B2 | 4/2008 | Heruth et al. |
| 7,395,113 B2 | 7/2008 | Heruth et al. |
| 7,415,308 B2 | 8/2008 | Gerber et al. |
| 7,447,545 B2 | 11/2008 | Heruth et al. |
| 7,468,040 B2 | 12/2008 | Hartley et al. |
| 7,491,181 B2 | 2/2009 | Heruth et al. |
| 7,542,803 B2 | 6/2009 | Heruth et al. |
| 7,580,752 B2 | 8/2009 | Gerber et al. |
| 7,590,453 B2 | 9/2009 | Heruth et al. |
| 7,590,455 B2 | 9/2009 | Heruth et al. |
| 7,717,848 B2 | 5/2010 | Heruth et al. |
| 7,787,946 B2 | 8/2010 | Stahmann et al. |
| 7,792,583 B2 | 9/2010 | Miesel et al. |
| 7,805,196 B2 | 9/2010 | Miesel et al. |
| 7,853,322 B2 | 12/2010 | Bourget et al. |
| 7,881,798 B2 | 2/2011 | Heruth et al. |
| 7,908,013 B2 | 3/2011 | Miesel et al. |

(56) References Cited

U.S. PATENT DOCUMENTS

| | | |
|---|---|---|
| 8,032,224 B2 | 10/2011 | Miesel et al. |
| 8,190,253 B2 | 5/2012 | Heruth et al. |
| 8,244,340 B2 | 8/2012 | Wu et al. |
| 8,308,661 B2 | 11/2012 | Miesel et al. |
| 8,335,568 B2 | 12/2012 | Heruth et al. |
| 8,337,431 B2 | 12/2012 | Heruth et al. |
| 8,725,244 B2 | 5/2014 | Miesel et al. |
| 8,744,587 B2 | 6/2014 | Miesel et al. |
| 9,205,264 B2 | 12/2015 | Heruth et al. |
| 2001/0031930 A1 | 10/2001 | Roizen et al. |
| 2001/0037067 A1 | 11/2001 | Tchou et al. |
| 2001/0041831 A1 | 11/2001 | Starkweather et al. |
| 2001/0049471 A1 | 12/2001 | Suzuki et al. |
| 2002/0077562 A1 | 6/2002 | Kalgren et al. |
| 2002/0091308 A1 | 7/2002 | Kipshidze et al. |
| 2002/0161412 A1 | 10/2002 | Sun et al. |
| 2002/0169485 A1 | 11/2002 | Pless et al. |
| 2002/0177882 A1 | 11/2002 | DiLorenzo |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0135917 A1 | 7/2003 | Ruane |
| 2003/0139692 A1 | 7/2003 | Barrey et al. |
| 2003/0149457 A1 | 8/2003 | Tcheng et al. |
| 2003/0153953 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171791 A1 | 9/2003 | KenKnight et al. |
| 2003/0195588 A1 | 10/2003 | Fischell et al. |
| 2003/0204219 A1 | 10/2003 | Gielen |
| 2003/0212445 A1 | 11/2003 | Weinberg |
| 2004/0002741 A1 | 1/2004 | Weinberg |
| 2004/0002742 A1 | 1/2004 | Florio |
| 2004/0015103 A1 | 1/2004 | Aminian et al. |
| 2004/0049132 A1 | 3/2004 | Barron et al. |
| 2004/0077995 A1 | 4/2004 | Ferek-Petric et al. |
| 2004/0088025 A1 | 5/2004 | Gesotti |
| 2004/0102814 A1 | 5/2004 | Sorenson et al. |
| 2004/0111040 A1 | 6/2004 | Ni et al. |
| 2004/0111041 A1 | 6/2004 | Ni et al. |
| 2004/0138719 A1* | 7/2004 | Cho ............ A61N 1/3601 607/42 |
| 2004/0199217 A1 | 10/2004 | Lee et al. |
| 2004/0215269 A1 | 10/2004 | Burnes et al. |
| 2004/0220621 A1 | 11/2004 | Zhou et al. |
| 2005/0021103 A1 | 1/2005 | DiLorenzo |
| 2005/0021104 A1 | 1/2005 | DiLorenzo |
| 2005/0039745 A1 | 2/2005 | Stahmann et al. |
| 2005/0042589 A1 | 2/2005 | Hatlestad et al. |
| 2005/0060001 A1 | 3/2005 | Singhal et al. |
| 2005/0061320 A1 | 3/2005 | Lee et al. |
| 2005/0065560 A1 | 3/2005 | Lee et al. |
| 2005/0076908 A1 | 4/2005 | Lee et al. |
| 2005/0080463 A1 | 4/2005 | Stahmann et al. |
| 2005/0085738 A1 | 4/2005 | Stahmann et al. |
| 2005/0113710 A1 | 5/2005 | Stahmann et al. |
| 2005/0115561 A1 | 6/2005 | Stahmann et al. |
| 2005/0119703 A1 | 6/2005 | DiLorenzo |
| 2005/0143617 A1 | 6/2005 | Auphan |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222626 A1 | 10/2005 | DiLorenzo |
| 2005/0222643 A1 | 10/2005 | Heruth et al. |
| 2005/0234514 A1 | 10/2005 | Heruth et al. |
| 2005/0234518 A1 | 10/2005 | Heruth et al. |
| 2005/0240086 A1 | 10/2005 | Akay |
| 2005/0240242 A1 | 10/2005 | DiLorenzo |
| 2005/0245790 A1 | 11/2005 | Bergfalk et al. |
| 2005/0245988 A1 | 11/2005 | Miesel |
| 2006/0224191 A1 | 10/2006 | DiLorenzo |
| 2006/0235472 A1 | 10/2006 | Goetz et al. |
| 2006/0293720 A1 | 12/2006 | DiLorenzo |
| 2007/0038265 A1 | 2/2007 | Tcheng et al. |
| 2007/0046408 A1 | 3/2007 | Shim |
| 2007/0073355 A1 | 3/2007 | DiLorenzo |
| 2007/0142862 A1 | 6/2007 | DiLorenzo |
| 2007/0255118 A1 | 11/2007 | Miesel et al. |
| 2008/0154111 A1 | 6/2008 | Wu et al. |
| 2009/0030263 A1 | 1/2009 | Heruth et al. |
| 2009/0036951 A1 | 2/2009 | Heruth et al. |
| 2013/0150921 A1 | 6/2013 | Singhal et al. |

FOREIGN PATENT DOCUMENTS

| | | |
|---|---|---|
| EP | 0564803 A1 | 10/1993 |
| EP | 0849715 B1 | 6/1998 |
| EP | 1195139 A1 | 4/2002 |
| EP | 1291036 A2 | 3/2003 |
| EP | 1308182 A2 | 5/2003 |
| EP | 1437159 A1 | 7/2004 |
| EP | 1322227 B1 | 12/2005 |
| GB | 2330912 A | 5/1999 |
| WO | 98/00197 A1 | 1/1998 |
| WO | 99/13765 A1 | 3/1999 |
| WO | 01/37930 A1 | 5/2001 |
| WO | 02/28282 A1 | 4/2002 |
| WO | 02/41771 A1 | 5/2002 |
| WO | 02/087433 A1 | 11/2002 |
| WO | 02/096512 A1 | 12/2002 |
| WO | 02/100267 A1 | 12/2002 |
| WO | 03/024325 A2 | 3/2003 |
| WO | 03/051356 A1 | 6/2003 |
| WO | 03/065891 A2 | 8/2003 |
| WO | 2005/028029 A2 | 3/2005 |
| WO | 2005/035050 A1 | 4/2005 |

OTHER PUBLICATIONS

"Bilateral Comparisons of the BiteStrip Bruxism Device and Masseter EMG Bruxism Events," downloaded from Internet Archive of www.quietsleep.com dated Jan. 29, 2005, http://web.archive.org/web/20041124075114/www.quietsleep.com/pdf/Bilateral+Comparisons.pdf, 1 pp.

"Bitestrip Flier," downloaded from Internet Archive of www.quietsleep.com dated Jan. 29, 2005, http://web.archive.org/web/20041124080003/www.quietsleep.com/pdf/bitestrip+Flier.pdf., 1 pp.

"Design Competition: Runners-Up for the Best Three Designs," EPN, vol. 26, No. 1, Jan. 2002, 1 pp.

"IBM & Citizen Watch develop Linux-based 'WatchPad'," http://www.linuxdevices.com/news/NS6580187845.html, Retrieved on Feb. 20, 2006, 5 pp.

"MiniMitter® Physiological and Behavioral Monitoring for Humans and Animals," http://www.minimitter.com/Products/Actiwatch, Retrieved on Feb. 20, 2006, 3 pp.

"The BiteStrip: A Novel Screener for Sleep Bruxism," downloaded from Internet Archive of www.quietsleep.com dated Jan. 29, 2005, http://http.web.archive.org/web/20041124072922/www.quietsleep.com/pdf/BiteStrip-+Novel+Screener.pdf., 1 pp.

"Watch," Wikipedia, the free encyclopedia, http://en.wikipedia.org/wiki/Watch, Feb. 20, 2006, 6 pp.

Aminian et al., "Physical Activity Monitoring Based on Accelerometry: Validation and Comparison with Video Observation," Medical & Biological Engineering & Computing, vol. 37, No. 2, Mar. 1999, pp. 304-308.

Amzica, "Physiology of Sleep and Wakefulness as it Relates to the Physiology of Epilepsy," Journal of Clinical Neurophysiology, American Clinical Neurophysiology Society, 19(6), Dec. 2002, pp. 488-503.

(56) References Cited

OTHER PUBLICATIONS

Antonini et al., "Deep brain stimulation and its effect on sleep in Parkinson's disease," Sleep Medicine, vol. 5, Issue 2, Mar. 2004, pp. 211-214.
Cicolin et al., "Effects of deep brain stimulation of the subthalamic nucleus on sleep architecture in parkinsonian patients," Sleep Medicine, vol. 5, Issue 2, Mar. 2004, pp. 207-210.
Criticare System Inc., -504DX Portable Pulse Oximeter, http://www.csiusa.com/504dx.html, Jan. 31, 2005, 4 pp.
Dinner, "Effect of Sleep of Epilepsy," Journal of Clinical Neurophysiology, American Clinical Neurophysiology Society, 19(6), Dec. 2002, pp. 504-513.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Societ, 19(6), Dec. 2002, pp. 514-521.
Goodrich et al., "The Prediction of Pain Using Measures of Sleep Quality," Pain Digest, Aug. 1998, pp. 23-25.
Greenberg, MD, Phd. et al., "Mechanisms and the current state of deep brain stimulation in neuropsychiatry," CNS Spectrums, vol. 8, No. 7, Jul. 2003, pp. 522-526.
Itamar Medical Information, http://itamar-medical.com/content.asp?id=31, Jan. 31, 2005, 2 pp.
Kassam, "2005 EDP Topic 'MK4': Tremor Data-Logger for Parkinson's Disease Patients," http://www.ee.ryerson.ca/~courses/edp2005/MK4.html, Feb. 20, 2006, 3 pp.
Kerr et al., "Analysis of the sit-stand-sit movement cycle in normal subjects," Clinical Bimechanics, vol. 12, No. 4, Jun. 1997, pp. 236-245.
MAP Medizin—Technologie GmbH, Poly-MESAM®, http://195.244.124.130/map/de/eng/map_med.nsf/cmsall/705643A3FCBE4188AC1256EF4 . . . , Jan. 31, 2005, 4 pp.
Medcare—A Global Leader in Sleep Diagnostics, Embletta Recording System, http://www.medcare.com/products/diagnostic/embletta/, Jan. 31, 2005, 2 pp.
Medcare—A Global Leader in Sleep Diagnostics, Somnologica for Embeltta, http://www.medcare.com/products/diagnostic/embletta/SomnoEmbletta/index.asp, Jan. 31, 2005, 1 pp.
Mendez et al., "Interactions Between Sleep and Epilepsy," Journal of Clinical Neurophysiology American Clinical Neurophysiology Society, 18(2), Mar. 2001, pp. 106-127.
Merlin, http://www.aha.ru/~pir/english/merlin, Jan. 31, 2005, 4 pp.
Oerlemans et al., "The prevalence of sleep disorders in patients with Parkinson's disease. A self-reported, community-based survey," Sleep Medicine, vol. 3, Issue 2, Mar. 2002, pp. 147-149.
Sleep Solutions—PR Newsire: Sleep Solutions Introduces NovaSom™ OSG™ for PSG . . . , http://www.sleep-solutions.com/press_room/novasom.htm, Jan. 31, 2005, 2 pp.
Sleep Strip & Bite Strip, http://www.quietsleep.com/snoringapnea/sleepstrip.htm, Jan. 31, 2005, 7 pp.
Smith, et al., "How do sleep disturbance and chronic pain inter-relate? Insights form the longitudinal and cognitive-behavioral clinical trials literature," Sleep Medicine Reviews, YSMRV 286, Jun. 19, 2003, 14 pp.
Smith, et al., "Presleep Cognitions in Patients with Insomnia Secondary to Chronic Pain," Journal of Behavioral Medicine, vol. 24, No. 1, Feb. 2001, pp. 93-114.
Snap® Laboratories, Product Fact Sheet, http://www.snaplab.com/mp_fact.htm, Jan. 31, 2005, 2 pp.
Tuisku, "Motor Activity Measured by Actometry in Neuropsychiatric Disorders," Department of Psychiatry, University of Helsinski, Helsinki, Finland, Dec. 13, 2002, 115 pp.
Prosecution History from U.S. Appl. No. 11/591,286, from Oct. 27, 2011 through Dec. 23, 2013, 268 pp.
Prosecution History from U.S. Appl. No. 10/826,925, from Jul. 3, 2007 through Aug. 11, 2009, 133 pp.
Prosecution History from U.S. Appl. No. 11/081,811, from May 30, 2008 through Jan. 19, 2016, 401 pp.
Prosecution History from U.S. Appl. No. 11/691,376, from Nov. 9, 2011 through Jun. 15, 2012, 119 pp.
Prosecution History from U.S. Appl. No. 12/723,501, from Nov. 5, 2012 through May 28, 2014, 78 pp.
Prosecution History from U.S. Appl. No. 14/276,516, from Feb. 25, 2015 through Aug. 5, 2015, 40 pp.
Prosecution History from U.S. Appl. No. 11/081,873, from Nov. 7, 2007 through Jul. 9, 2008, 45 pp.
Prosecution History from U.S. Appl. No. 11/691,413, from Mar. 12, 2010 through May 17, 2011, 73 pp.
Prosecution History from U.S. Appl. No. 12/248,622, from May 20, 2010 through Jul. 30, 2015, 112 pp.
Prosecution History from U.S. Appl. No. 12/248,609, from Aug. 5, 2010 through Jul. 30, 2015, 84 pp.
Prosecution History from U.S. Appl. No. 10/825,953, from Jul. 5, 2006 through Nov. 29, 2007, 97 pp.
Prosecution History from U.S. Appl. No. 11/081,155, from Apr. 4, 2008 through May 5, 2009, 35 pp.
Prosecution History from U.S. Appl. No. 11/691,430, from Feb. 5, 2010 through Sep. 28, 2010, 34 pp.
Prosecution History from U.S. Appl. No. 12/544,727, from May 3, 2012 through Sep. 24, 2012, 31 pp.
Prosecution History from U.S. Appl. No. 10/825,955, from May 31, 2006 through Oct. 9, 2008, 169 pp.
Prosecution History from U.S. Appl. No. 11/081,857, from Oct. 11, 2007 through May 27, 2010, 140 pp.
Prosecution History from U.S. Appl. No. 11/691,425, from Sep. 22, 2011 through Jul. 9, 2012, 87 pp.
Prosecution History from U.S. Appl. No. 12/351,414, from Oct. 13, 2009 through Sep. 20, 2012, 59 pp.
Van Dam, et al., "Measuring physical activity in patients after surgery for a malignant tumour in the leg," The Journal of Bone & Joint Surgery, vol. 83-B, No. 7, Sep. 2001, pp. 1015-1019.
Response to Office Action dated Oct. 27, 2016, from U.S. Appl. No. 14/247,923, filed Jan. 25, 2017, 20 pp.

* cited by examiner

COLLECTING SLEEP QUALITY INFORMATION VIA A MEDICAL DEVICE

This application is a continuation of U.S. patent application Ser. No. 14/276,516, filed May 13, 2014 which is a continuation of U.S. patent application Ser. No. 12/723,501, filed Mar. 12, 2010 (now U.S. Pat. No. 8,758,242), which is a divisional of U.S. patent application Ser. No. 10/826,925, filed Apr. 15, 2004 (now U.S. Pat. No. 7,717,848), which claims the benefit of U.S. Provisional Application No. 60/553,783, filed Mar. 16, 2004. The entire content of each of these applications is incorporated by reference herein.

TECHNICAL FIELD

The invention relates to medical devices and, more particularly, to medical devices that monitor physiological parameters.

BACKGROUND

In some cases, an ailment that a patient has may affect the quality of the patient's sleep. For example, chronic pain may cause a patient to have difficulty falling asleep, and may disturb the patient's sleep, e.g., cause the patient to wake. Further, chronic pain may cause the patient to have difficulty achieving deeper sleep states, such as one or more of the nonrapid eye movement (NREM) sleep states. Other ailments that may negatively affect patient sleep quality include movement disorders, psychological disorders, sleep apnea, congestive heart failure, gastrointestinal disorders and incontinence. In some cases, these ailments are treated via an implantable medical device (IMD), such as an implantable stimulator or drug delivery device.

Further, in some cases, poor sleep quality may increase the symptoms experienced by a patient due to an ailment. For example, poor sleep quality has been linked to increased pain symptoms in chronic pain patients. The link between poor sleep quality and increased symptoms is not limited to ailments that negatively impact sleep quality, such as those listed above. Nonetheless, the condition of a patient with such an ailment may progressively worsen when symptoms disturb sleep quality, which in turn increases the frequency and/or intensity of symptoms.

SUMMARY

In general, the invention is directed to techniques for collecting information that relates to the quality of patient sleep via a medical device, such as an implantable medical device (IMD). In particular, values for one or more metrics that indicate the quality of the patient's sleep are determined based on physiological parameters monitored by a medical device. In some embodiments, sleep quality information is presented to a user based on the sleep quality metric values. A clinician, for example, may use the presented sleep quality information to evaluate the effectiveness of therapy delivered to the patient by the medical device, to adjust the therapy delivered by the medical device, or to prescribe a therapy not delivered by the medical device in order to improve the quality of the patient's sleep.

The medical device monitors one or more physiological parameters of the patient. Example physiological parameters that the medical device may monitor include activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, melatonin level within one or more bodily fluids, and galvanic skin response. In order to monitor one or more of these parameters, the medical device may include, be coupled to one or more sensors, each of which generates a signal as a function of one or more of these physiological parameters.

The medical device may determine a value of one or more sleep quality metrics based on the one or more monitored physiological parameters, and/or the variability of one or more of the monitored physiological parameters. In other embodiments, the medical device records values of the one or more physiological parameters, and provides the physiological parameter values to a programming device, such as a clinician programming device or a patient programming device. In such embodiments, the programming device determines values of one or more sleep quality metrics based on the physiological parameter values received from the medical device and/or the variability of one or more of the physiological parameters. The medical device may provide the recorded physiological parameter values to the programming device in real time, or may provide physiological parameter values recorded over a period of time to the programming device when interrogated by the programming device.

Sleep efficiency and sleep latency are example sleep quality metrics for which a medical device or programming device may determine values. Sleep efficiency may be measured as the percentage of time while the patient is attempting to sleep that the patient is actually asleep. Sleep latency may be measured as the amount of time between a first time when the patient begins attempting to fall asleep and a second time when the patient falls asleep, and thereby indicates how long a patient requires to fall asleep.

The time when the patient begins attempting to fall asleep may be determined in a variety of ways. For example, the medical device may receive an indication from the patient that the patient is trying to fall asleep, e.g., via a patient programming device in embodiments in which the medical device is an implantable medical device. In other embodiments, the medical device may monitor the activity level of the patient, and the time when the patient is attempting to fall asleep may be identified by determining whether the patient has remained inactive for a threshold period of time, and identifying the time at which the patient became inactive. In still other embodiments, the medical device may monitor patient posture, and the medical device or a programming device may identify the time when the patient is recumbent, e.g., lying down, as the time when the patient is attempting to fall asleep. In these embodiments, the medical device may also monitor patient activity, and either the medical device or the programming device may confirm that the patient is attempting to sleep based on the patient's activity level.

As another example, the medical device may determine the time at which the patient begins attempting to fall asleep based on the level of melatonin within one or more bodily fluids, such as the patient's blood, cerebrospinal fluid (CSF), or interstitial fluid. The medical device may also determine a melatonin level based on metabolites of melatonin located in the saliva or urine of the patient. Melatonin is a hormone secreted by the pineal gland into the bloodstream and the CSF as a function of exposure of the optic nerve to light, which synchronizes the patient's circadian rhythm. In particular, increased levels of melatonin during evening hours may cause physiological changes in the patient, which, in turn, may cause the patient to attempt to fall asleep. The medical device may, for example, detect an increase in the level of melatonin, and estimate the time that the patient will attempt to fall asleep based on the detection.

The time at which the patient has fallen asleep may be determined based on the activity level of the patient and/or one or more of the other physiological parameters that may be monitored by the medical device as indicated above. For example, a discernable change, e.g., a decrease, in one or more physiological parameters, or the variability of one or more physiological parameters, may indicate that the patient has fallen asleep. In some embodiments, a sleep probability metric value may be determined based on a value of a physiological parameter monitored by the medical device. In such embodiments, the sleep probability metric value may be compared to a threshold to identify when the patient has fallen asleep. In some embodiments, a plurality of sleep probability metric values are determined based on a value of each of a plurality of physiological parameters, the sleep probability values are averaged or otherwise combined to provide an overall sleep probability metric value, and the overall sleep probability metric value is compared to a threshold to identify the time that the patient falls asleep.

Other sleep quality metrics that may be determined include total time sleeping per day, the amount or percentage of time sleeping during nighttime or daytime hours per day, and the number of apnea and/or arousal events per night. In some embodiments, which sleep state the patient is in, e.g., rapid eye movement (REM), or one of the nonrapid eye movement (NREM) states (S1, S2, S3, S4) may be determined based on physiological parameters monitored by the medical device, and the amount of time per day spent in these various sleep states may be a sleep quality metric. Because they provide the most "refreshing" type of sleep, the amount of time spent in one or both of the S3 and S4 sleep states, in particular, may be determined as a sleep quality metric. In some embodiments, average or median values of one or more sleep quality metrics over greater periods of time, e.g., a week or a month, may be determined as the value of the sleep quality metric. Further, in embodiments in which values for a plurality of the sleep quality metrics are determined, a value for an overall sleep quality metric may be determined based on the values for the plurality of individual sleep quality metrics.

In some embodiments, the medical device delivers a therapy. At any given time, the medical device delivers the therapy according to a current set of therapy parameters. For example, in embodiments in which the medical device is a neurostimulator, a therapy parameter set may include a pulse amplitude, a pulse width, a pulse rate, a duty cycle, and an indication of active electrodes. Different therapy parameter sets may be selected, e.g., by the patient via a programming device or a the medical device according to a schedule, and parameters of one or more therapy parameter sets may be adjusted by the patient to create new therapy parameter sets. In other words, over time, the medical device delivers the therapy according to a plurality of therapy parameter sets.

In embodiments in which the medical device determines sleep quality metric values, the medical device may identify the current therapy parameter set when a value of one or more sleep quality metrics is collected, and may associate that value with the therapy parameter set. For example, for each available therapy parameter set the medical device may store a representative value of each of one or more sleep quality metrics in a memory with an indication of the therapy programs with which that representative value is associated. A representative value of sleep quality metric for a therapy parameter set may be the mean or median of collected sleep quality metric values that have been associated with that therapy parameter set. In other embodiments in which a programming device determines sleep quality metric values, the medical device may associate recorded physiological parameter values with the current therapy parameter set in the memory.

A programming device according to the invention may be capable of wireless communication with the medical device, and may receive sleep quality metric values or recorded physiological parameter values from the medical device. In either case, when the programming device either receives or determines sleep quality metric values, the programming device may provide sleep quality information to a user based on the sleep quality metric values. For example, the programming device may be a patient programmer, and may provide a message to the patient related to sleep quality. The patient programmer may, for example, suggest that the patient visit a clinician for prescription of sleep medication or for an adjustment to the therapy delivered by the medical device. As other examples, the patient programmer may suggest that the patient increase the intensity of therapy delivered by the medical device during nighttime hours relative to previous nights, or select a different therapy parameter set for use during sleep than the patient had selected during previous nights. Further, the patient programmer may provide a message that indicates the quality of sleep to the patient to, for example, provide the patient with an objective indication of whether his or her sleep quality is good, adequate, or poor.

In other embodiments, the programming device is a clinician programmer that presents information relating to the quality of the patient's sleep to a clinician. The clinician programmer may present, for example, a trend diagram of values of one or more sleep quality metrics over time. As other examples, the clinician programmer may present a histogram or pie chart illustrating percentages of time that a sleep quality metric was within various value ranges.

In embodiments in which the medical device associates sleep quality metric values or physiological parameter values with therapy parameter sets, the programming device may receive representative values for one or more sleep quality metrics or the physiological parameter values from the medical device, and information identifying the therapy parameter set with which the representative values are associated. In embodiments in which the programming device receives physiological parameter values from a medical device, the programming device may determine sleep quality metric values associated with the plurality of parameter sets based on the physiological parameter values, and representative sleep quality metric values for each of the therapy parameter sets based on the sleep quality metric values associated with the therapy parameter sets. In some embodiments, the programming device may determine the variability of one or more of the physiological parameters based on the physiological parameter values received from the medical device, and may determine sleep quality metric values based on the physiological parameter variabilities.

The programming device may display a list of the therapy parameter sets to the clinician ordered according to their associated representative sleep quality metric values. Such a list may be used by the clinician to identify effective or ineffective therapy parameter sets. Where a plurality of sleep quality metric values are determined, the programming device may order the list according to values of a user-selected one of the sleep quality metrics.

In other embodiments, a system according to the invention does not include a programming device. For example, an external medical device according to the invention may include a display, determine sleep quality metric values, and display sleep quality information to a user via the display based on the sleep quality metric values.

In one embodiment, the invention is directed to a method in which at least one physiological parameter of a patient is monitored via a medical device that delivers a therapy to the patient. A value of a metric that is indicative of sleep quality is determined based on the at least one physiological parameter. A current therapy parameter set is identified, and the sleep quality metric value is associated with the current therapy parameter set.

In another embodiment, the invention is directed to a medical system comprising a medical device and a processor. The medical device delivers a therapy to a patient, and monitors at least one physiological parameter of a patient based on a signal received from at least one sensor. The processor determines a value of a metric that is indicative of sleep quality based on the at least one physiological parameter, identifies a current therapy parameter set, and associates the sleep quality metric value with the current therapy parameter set.

In another embodiment, the invention is directed to a medical system comprising means for monitoring at least one physiological parameter of a patient, means for determining a value of a metric that is indicative of sleep quality based on the at least one physiological parameter, means for identifying a current therapy parameter set used by a medical device to delivery therapy to the patient, and means for associating the sleep quality metric value with the current therapy parameter set.

In another embodiment, the invention is directed to a medical system comprising an implantable medical device and an external programming device including a display. The implantable medical device delivers a therapy to a patient, monitors at least one physiological parameter of the patient, and determines a plurality of values of a metric that is indicative of sleep quality based on the at least one physiological parameter. The external programming device receives sleep quality metric values from the implantable medical device, and presents sleep quality information to a user via the display based on the sleep quality metric values.

In another embodiment, the invention is directed to a programming device comprising a telemetry circuit, a user interface including a display, and a processor. The processor receives sleep quality metric values from a medical device via the telemetry circuit, and presents sleep quality information to a user via the display based on the sleep quality metric values.

In another embodiment, the invention is directed to a computer-readable medium comprising program instructions. The program instructions cause a programmable processor to receive sleep quality metric values from a medical device, and present sleep quality information to a user via a display based on the sleep quality metric values.

In another embodiment, the invention is directed to a method in which a plurality of signals are monitored, each of the signals generated by a sensor as a function of at least one physiological parameter of a patient. When the patient is attempting to sleep is identified. When the patient is asleep is identified based on at least one of the signals. A value of a metric that is indicative of sleep quality is determined based on the identifications of when the patient is attempting to sleep and asleep.

In another embodiment, the invention is directed to a medical system comprising a plurality of sensors and a processor. Each of the plurality of sensors generates a signal as a function of at least one physiological parameter of a patient. The processor monitors the signals generated by the sensors, identifies when the patient is attempting to sleep, identifies when the patient is asleep based on at least one of the signals, and determines a value of a metric that is indicative of sleep quality based on the identifications of when the patient is attempting to sleep and asleep.

The invention may be capable of providing one or more advantages. For example, by providing information related to the quality of a patient's sleep to a clinician and/or the patient, a system according to the invention can improve the course of treatment of an ailment of the patient, such as chronic pain. Using the sleep quality information provided by the system, the clinician and/or patient can, for example, make changes to the therapy provided by a medical device in order to better address symptoms which are disturbing the patient's sleep. Further, a clinician may choose to prescribe a therapy that will improve the patient's sleep, such as a sleep inducing medication, in situations where poor sleep quality is increasing symptoms experienced by the patient.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
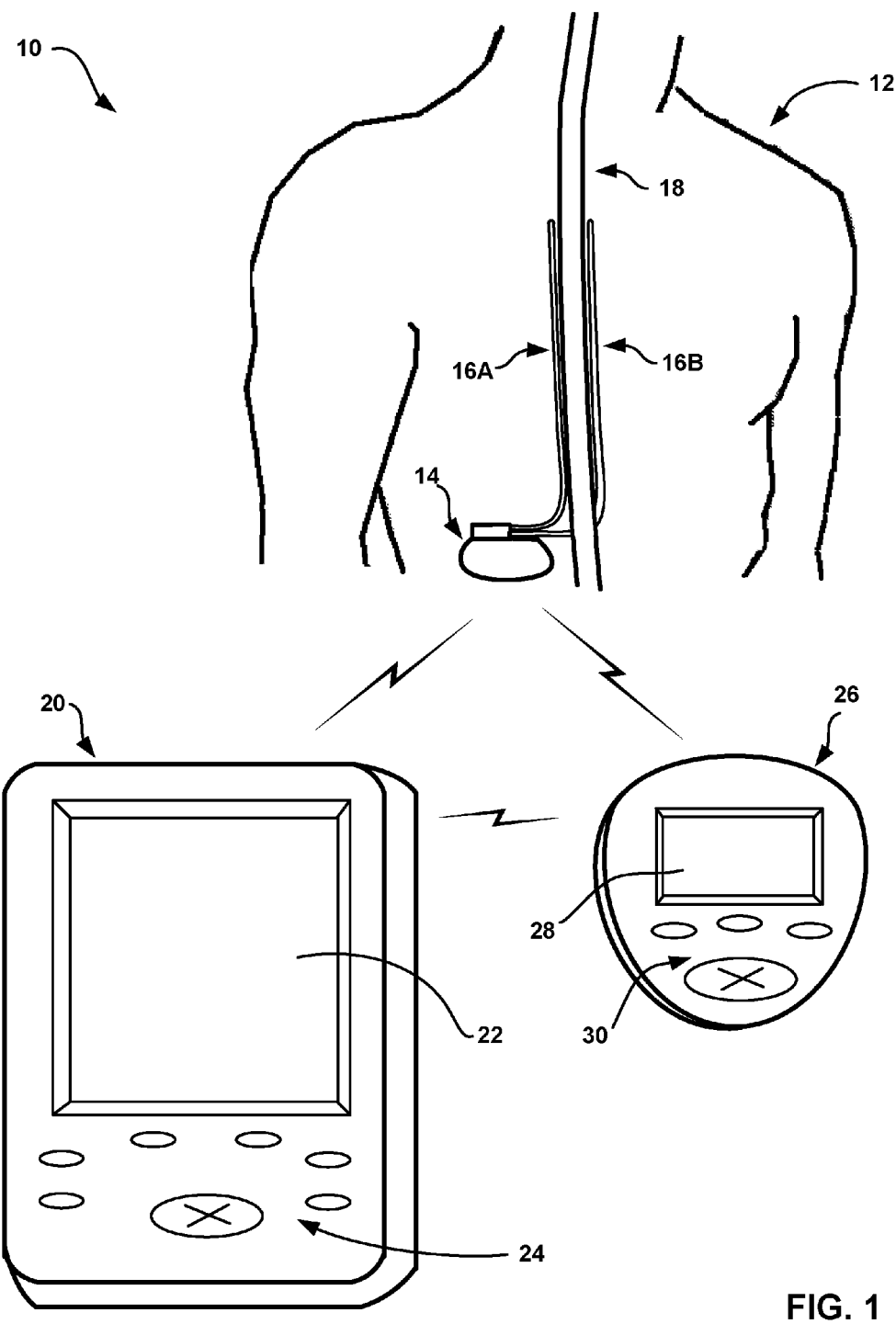
FIG. 1 is a conceptual diagram illustrating an example system that includes an implantable medical device that collects sleep quality information according to the invention.

FIG. 1 is a conceptual diagram illustrating an example system 10 that includes an implantable medical device (IMD) 14 that collects information relating to the quality of sleep experienced by a patient 12 according to the invention. Sleep quality information collected by IMD 14 is provided to a user, such as a clinician or the patient. Using the sleep quality information collected by IMD 14, a current course of therapy for an ailment of patient 12 may be evaluated, and an improved course of therapy for the ailment may be identified.

In the illustrated example system 10, IMD 14 takes the form of an implantable neurostimulator that delivers neurostimulation therapy in the form of electrical pulses to patient 12. However, the invention is not limited to implementation via an implantable neurostimulator. For example, in some embodiments of the invention, an implantable pump or implantable cardiac rhythm management device, such as a pacemaker, may collect sleep quality information. Further, the invention is not limited to implementation via an IMD. In other words, any implantable or external medical device may collect sleep quality information according to the invention.

In the example of FIG. 1, IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown) or stomach (not shown), and IMD 14 may deliver neurostimulation therapy to treat incontinence or gastroparesis.

IMD 14 delivers therapy according to a set of therapy parameters, i.e., a set of values for a number of parameters that define the therapy delivered according to that therapy parameter set. In embodiments where IMD 14 delivers neurostimulation therapy in the form of electrical pulses, the parameters in each parameter set may include voltage or current pulse amplitudes, pulse widths, pulse rates, and the like. Further, each of leads 16 includes electrodes (not shown in FIG. 1), and a therapy parameter set may include information identifying which electrodes have been selected for delivery of pulses, and the polarities of the selected electrodes. Therapy parameter sets used by IMD 14 may include a number of parameter sets programmed by a clinician (not shown), and parameter sets representing adjustments made by patient 12 to these preprogrammed sets.

System 10 also includes a clinician programmer 20. A clinician (not shown) may use clinician programmer 20 to program therapy for patient 12, e.g., specify a number of therapy parameter sets and provide the parameter sets to IMD 14. The clinician may also use clinician programmer 20 to retrieve information collected by IMD 14. The clinician may use clinician programmer 20 to communicate with IMD 14 both during initial programming of IMD 14, and for collection of information and further programming during follow-up visits.

Clinician programmer 20 may, as shown in FIG. 1, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

System 10 also includes a patient programmer 26, which also may, as shown in FIG. 1, be a handheld computing device. Patient 12 may use patient programmer 26 to control the delivery of therapy by IMD 14. For example, using patient programmer 26, patient 12 may select a current therapy parameter set from among the therapy parameter sets preprogrammed by the clinician, or may adjust one or more parameters of a preprogrammed therapy parameter set to arrive at the current therapy parameter set.

Patient programmer 26 may include a display 28 and a keypad 30, to allow patient 12 to interact with patient programmer 26. In some embodiments, display 28 may be a touch screen display, and patient 12 may interact with patient programmer 26 via display 28. Patient 12 may also interact with patient programmer 26 using peripheral pointing devices, such as a stylus, mouse, or the like.

However, clinician and patient programmers 20, 26 are not limited to the hand-held computer embodiments illustrated in FIG. 1. Programmers 20, 26 according to the invention may be any sort of computing device. For example, a programmer 20, 26 according to the invention may be a tablet-based computing device, a desktop computing device, or a workstation.

IMD 14, clinician programmer 20 and patient programmer 26 may, as shown in FIG. 1, communicate via wireless communication. Clinician programmer 20 and patient programmer 26 may, for example, communicate via wireless communication with IMD 14 using radio frequency (RF) telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

As mentioned above, IMD 14 collects information relating to the quality of sleep experienced by patient 12. Specifically, as will be described in greater detail below, IMD 14 monitors one or more physiological parameters of patient 12, and determines values for one or more metrics that indicate the quality of sleep based on values of the physiological parameters. Example physiological parameters that IMD 14 may monitor include activity level, posture, heart rate, respiration rate, respiratory volume, blood pressure, blood oxygen saturation, partial pressure of oxygen within blood, partial pressure of oxygen within cerebrospinal fluid (CSF), muscular activity, core temperature, arterial blood flow, and the level of melatonin within one or more bodily fluids. In some external medical device embodiments of the invention, galvanic skin response may additionally or alternatively be monitored. Further, in some embodiments, IMD 14 additionally or alternatively monitors the variability of one or more of these parameters. In order to monitor one or more of these parameters, IMD 14 may include or be coupled to one or more sensors (not shown in FIG. 1), each of which generates a signal as a function of one or more of these physiological parameters.

For example, IMD 14 may determine sleep efficiency and/or sleep latency values. Sleep efficiency and sleep latency are example sleep quality metrics. IMD 14 may measure sleep efficiency as the percentage of time while patient 12 is attempting to sleep that patient 12 is actually asleep. IMD 14 may measure sleep latency as the amount of time between a first time when patient 12 begins attempting to fall asleep and a second time when patient 12 falls asleep.

IMD 14 may identify the time at which patient begins attempting to fall asleep in a variety of ways. For example, IMD 14 may receive an indication from the patient that the patient is trying to fall asleep via patient programmer 26. In other embodiments, IMD 14 may monitor the activity level of patient 12, and identify the time when patient 12 is attempting to fall asleep by determining whether patient 12 has remained inactive for a threshold period of time, and identifying the time at which patient 12 became inactive. In still other embodiments, IMD 14 may monitor the posture of patient 12, and may identify the time when the patient 12 becomes recumbent, e.g., lies down, as the time when patient 12 is attempting to fall asleep. In these embodiments, IMD 14 may also monitor the activity level of patient 12, and confirm that patient 12 is attempting to sleep based on the activity level.

As another example, IMD 14 may determine the time at which patient 12 is attempting to fall asleep based on the level of melatonin within one or more bodily fluids of patient 12, such as the patient's blood, cerebrospinal fluid (CSF), or interstitial fluid. IMD 14 may also determine a melatonin level based on metabolites of melatonin located in the saliva or urine of the patient. Melatonin is a hormone secreted by the pineal gland into the bloodstream and the CSF as a function of exposure of the optic nerve to light, which synchronizes the patient's circadian rhythm. In particular, increased levels of melatonin during evening hours may cause physiological changes in patient 12, which, in turn, may cause patient 12 to attempt to fall asleep.

IMD 14 may, for example, detect an increase in the level of melatonin in a bodily fluid, and estimate the time that patient 12 will attempt to fall asleep based on the detection. For example, IMD 14 may compare the melatonin level or rate of change in the melatonin level to a threshold level, and identify the time that threshold value is exceeded. IMD 14 may identify the time that patient 12 is attempting to fall asleep as the time that the threshold is exceeded, or some amount of time after the threshold is exceeded.

IMD 14 may identify the time at which patient 12 has fallen asleep based on the activity level of the patient and/or one or more of the other physiological parameters that may be monitored by IMD 14 as indicated above. For example, IMD 14 may identify a discernable change, e.g., a decrease, in one or more physiological parameters, or the variability of one or more physiological parameters, which may indicate that patient 12 has fallen asleep. In some embodiments, IMD 14 determines a sleep probability metric value based on a value of a physiological parameter monitored by the medical device. In such embodiments, the sleep probability metric value may be compared to a threshold to identify when the patient has fallen asleep. In some embodiments, a sleep probability metric value is determined based on a value of each of a plurality of physiological parameters, the sleep probability values are averaged or otherwise combined to provide an overall sleep probability metric value, and the overall sleep probability metric value is compared to a threshold to identify the time that the patient falls asleep.

Other sleep quality metrics include total time sleeping per day, and the amount or percentage of time sleeping during nighttime or daytime hours per day. In some embodiments, IMD 14 may be able to detect arousal events and apneas occurring during sleep based on one or more monitored physiological parameters, and the number of apnea and/or arousal events per night may be determined as a sleep quality metric. Further, in some embodiments IMD 14 may be able to determine which sleep state patient 12 is in based on one or more monitored physiological parameters, e.g., rapid eye movement (REM), S1, S2, S3, or S4, and the amount of time per day spent in these various sleep states may be a sleep quality metric.

The S3 and S4 sleep states may be of particular importance to the quality of sleep experienced by patient 12. Interruption from reaching these states, or inadequate time per night spent in these states, may cause patient 12 to not feel rested. For this reason, the S3 and S4 sleep states are believed to provide the "refreshing" part of sleep.

In some cases, interruption from reaching the S3 and S4 sleep states, or inadequate time per night spent in these states has been demonstrated to cause normal subjects to exhibit some symptoms of fibromyalgia. Also, subjects with fibromyalgia usually do not reach these sleep states. For these reasons, in some embodiments, IMD 14 may determine an amount or percentage of time spent in one or both of the S3 and S4 sleep states as a sleep quality metric.

In some embodiments, IMD 14 may determine average or median values of one or more sleep quality metrics over greater periods of time, e.g., a week or a month, as the value of the sleep quality metric. Further, in embodiments in which IMD 14 collects values for a plurality of the sleep quality metrics identified above, IMD 14 may determine a value for an overall sleep quality metric based on the collected values for the plurality of sleep quality metrics. IMD 14 may determine the value of an overall sleep quality metric by applying a function or look-up table to a plurality of sleep quality metric values, which may also include the application of weighting factors to one or more of the individual sleep quality metric values.

In some embodiments, IMD 14 may identify the current set of therapy parameters when a value of one or more sleep quality metrics is collected, and may associate that value with the current therapy parameter sets. For example, for each of a plurality therapy parameter sets used over time by IMD 14 to deliver therapy to patient 12, IMD 14 may store a representative value of each of one or more sleep quality metrics in a memory with an indication of the therapy parameter set with which that representative value is associated. A representative value of sleep quality metric for a therapy parameter set may be the mean or median of collected sleep quality metric values that have been associated with that therapy parameter set.

One or both of programmers 20, 26 may receive sleep quality metric values from IMD 14, and may provide sleep quality information to a user based on the sleep quality metric values. For example, patient programmer 26 may provide a message to patient 12, e.g., via display 28, related to sleep quality based on received sleep quality metric values. Patient programmer 26 may, for example, suggest that patient 12 visit a clinician for prescription of sleep medication or for an adjustment to the therapy delivered by IMD 14. As other examples, patient programmer 26 may suggest that patient 12 increase the intensity of therapy delivered by IMD 14 during nighttime hours relative to previous nights, or select a different therapy parameter set for use by IMD 14 than the patient had selected during previous nights. Further, patient programmer 26 may report the quality of the patient's sleep to patient 12 to, for example, provide patient 12 with an objective indication of whether his or her sleep quality is good, adequate, or poor.

Clinician programmer 20 may receive sleep quality metric values from IMD 14, and present a variety of types of sleep information to a clinician, e.g., via display 22, based on the sleep quality metric values. For example, clinician programmer 20 may present a graphical representation of the sleep quality metric values, such as a trend diagram of values of one or more sleep quality metrics over time, or a histogram or pie chart illustrating percentages of time that a sleep quality metric was within various value ranges.

In embodiments in which IMD 14 associates sleep quality metric values with therapy parameter sets, clinician programmer 20 may receive representative values for one or more sleep quality metrics from IMD 14 and information identifying the therapy parameter sets with which the representative values are associated. Using this information, clinician programmer 20 may display a list of the therapy parameter sets to the clinician ordered according to their associated representative sleep quality metric values. The clinician may use such a list to identify effective or ineffective therapy parameter sets. Where a plurality of sleep quality metric values are collected, clinician programmer 20 may order the list according to values of a user-selected one of the sleep quality metrics. In this manner, the clinician may quickly identify the therapy parameter sets producing the best results in terms of sleep quality.

Figure 2:
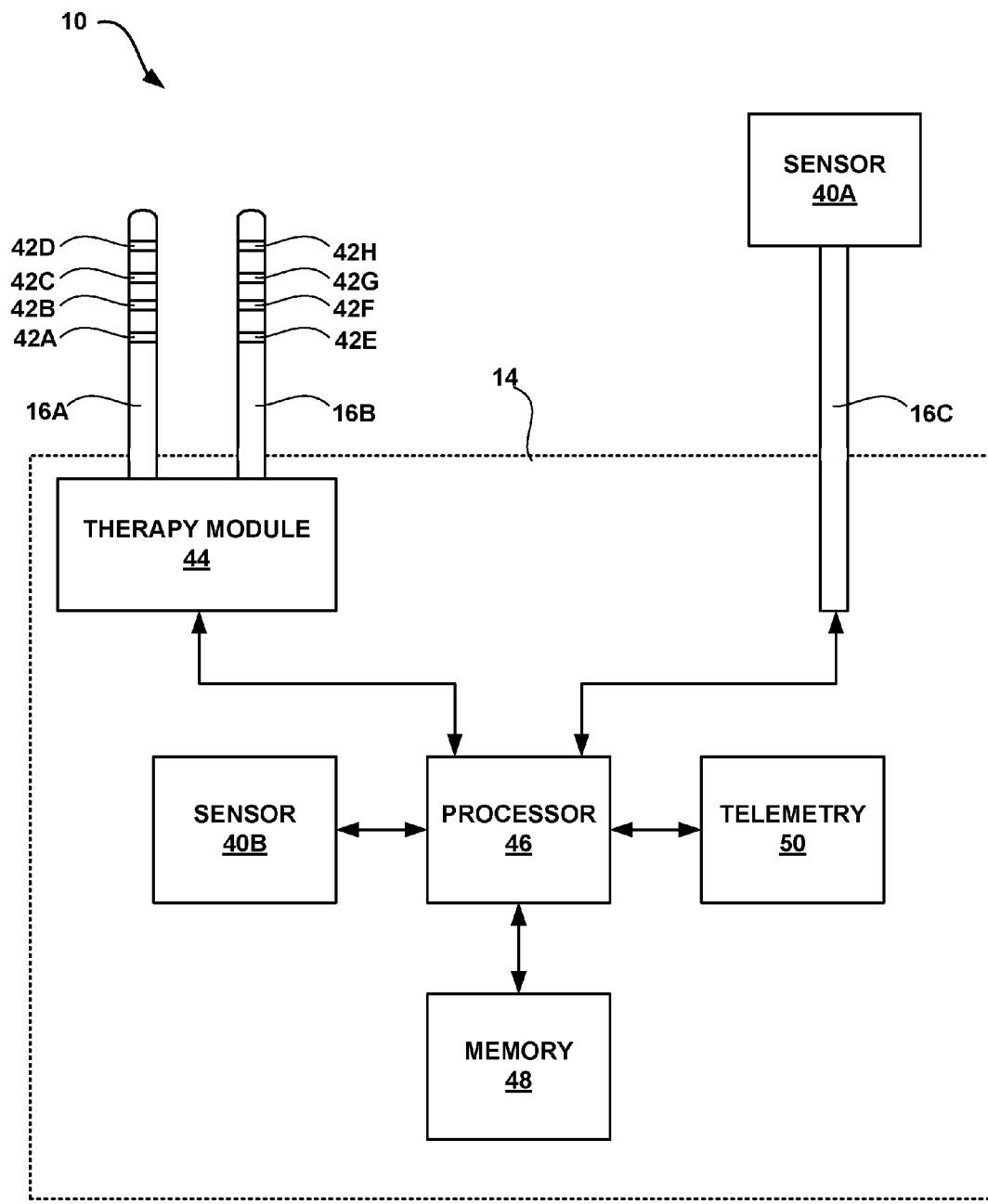
FIG. 2 is a block diagram further illustrating the example system and implantable medical device of FIG. 1.

FIG. 2 is a block diagram further illustrating system 10. In particular, FIG. 2 illustrates an example configuration of IMD 14 and leads 16A and 16B. FIG. 2 also illustrates sensors 40A and 40B (collectively "sensors 40") that generate signals as a function of one or more physiological parameters of patient 12. As will be described in greater detail below, IMD 14 monitors the signals to determine values for one or more metrics that are indicative of sleep quality.

IMD 14 may deliver neurostimulation therapy via electrodes 42A-D of lead 16A and electrodes 42E-H of lead 16B (collectively "electrodes 42"). Electrodes 42 may be ring electrodes. The configuration, type and number of electrodes 42 illustrated in FIG. 2 are merely exemplary. For example, leads 16A and 16B may each include eight electrodes 42, and the electrodes 42 need not be arranged linearly on each of leads 16A and 16B.

Electrodes 42 are electrically coupled to a therapy delivery module 44 via leads 16A and 16B. Therapy delivery module 44 may, for example, include an output pulse generator coupled to a power source such as a battery. Therapy delivery module 44 may deliver electrical pulses to patient 12 via at least some of electrodes 42 under the control of a processor 46, which controls therapy delivery module 44 to deliver neurostimulation therapy according to to a current therapy parameter set. However, the invention is not limited to implantable neurostimulator embodiments or even to IMDs that deliver electrical stimulation. For example, in some embodiments a therapy delivery module 44 of an IMD may include a pump, circuitry to control the pump, and a reservoir to store a therapeutic agent for delivery via the pump.

Processor 46 may include a microprocessor, a controller, a digital signal processor (DSP), an application specific integrated circuit (ASIC), a field-programmable gate array (FPGA), discrete logic circuitry, or the like. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 48 stores program instructions that, when executed by processor 46, cause IMD 14 and processor 46 to perform the functions attributed to them herein.

Each of sensors 40 generates a signal as a function of one or more physiological parameters of patient 12. IMD 14 may include circuitry (not shown) that conditions the signals generated by sensors 40 such that they may be analyzed by processor 46. For example, IMD 14 may include one or more analog to digital converters to convert analog signals generated by sensors 40 into digital signals usable by processor 46, as well as suitable filter and amplifier circuitry. Although shown as including two sensors 40, system 10 may include any number of sensors.

Further, as illustrated in FIG. 2, sensors 40 may be included as part of IMD 14, or coupled to IMD 14 via leads 16. Sensors 40 may be coupled to IMD 14 via therapy leads 16A and 16B, or via other leads 16, such as lead 16C depicted in FIG. 2. In some embodiments, a sensor 40 located outside of IMD 14 may be in wireless communication with processor 46.

As discussed above, exemplary physiological parameters of patient 12 that may be monitored by IMD 14 to determine values of one or more sleep quality metrics include activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and the level of melatonin within a bodily fluid of patient 12. Further, as discussed above, in some external medical device embodiments of the invention, galvanic skin response may additionally or alternatively be monitored. Sensors 40 may be of any type known in the art capable of generating a signal as a function of one or more of these parameters.

In some embodiments, in order to determine one or more sleep quality metric values, processor 46 determines when patient 12 is attempting to fall asleep. For example, processor 46 may identify the time that patient begins attempting to fall asleep based on an indication received from patient 12, e.g., via clinician programmer 20 and a telemetry circuit 50. In other embodiments, processor 46 identifies the time that patient 12 begins attempting to fall asleep based on the activity level of patient 12.

In such embodiments, IMD 14 may include one or more sensors 40 that generate a signal as a function of patient activity. For example, sensors 40 may include one or more accelerometers, gyros, mercury switches, or bonded piezoelectric crystals that generates a signal as a function of patient activity, e.g., body motion, footfalls or other impact events, and the like. Processor 46 may identify a time when the activity level of patient 12 falls below a threshold activity level value stored in memory 48, and may determine whether the activity level remains substantially below the threshold activity level value for a threshold amount of time stored in memory 48. In other words, patient 12 remaining inactive for a sufficient period of time may indicate that patient 12 is attempting to fall asleep. If processor 46 determines that the threshold amount of time is exceeded, processor 46 may identify the time at which the activity level fell below the threshold activity level value as the time that patient 12 began attempting to fall asleep.

In some embodiments, processor 46 determines whether patient 12 is attempting to fall asleep based on whether patient 12 is or is not recumbent, e.g., lying down. In such embodiments, sensors 40 may include a plurality of accelerometers, gyros, or magnetometers oriented orthogonally that generate signals which indicate the posture of patient 12. In addition to being oriented orthogonally with respect to each other, each of sensors 40 used to detect the posture of patient 12 may be generally aligned with an axis of the body of patient 12. In exemplary embodiments, IMD 14 includes three orthogonally oriented posture sensors 40.

When sensors 40 include accelerometers, for example, that are aligned in this manner, processor 46 may monitor the magnitude and polarity of DC components of the signals generated by the accelerometers to determine the orientation of patient 12 relative to the Earth's gravity, e.g., the posture of patient 12. In particular, the processor 46 may compare the DC components of the signals to respective threshold values stored in memory 48 to determine whether patient 12 is or is not recumbent. Further information regarding use of orthogonally aligned accelerometers to determine patient posture may be found in a commonly assigned U.S. Pat. No. 5,593,431, which issued to Todd J. Sheldon.

In some embodiments, processor 46 considers both the posture and the activity level of patient 12 when determining whether patient 12 is attempting to fall asleep. For example, processor 46 may determine whether patient 12 is attempting to fall asleep based on a sufficiently long period of sub-threshold activity, as described above, and may identify the time that patient began attempting to fall asleep as the time when patient 12 became recumbent.

In other embodiments, processor 46 determines when patient 12 is attempting to fall asleep based on the level of melatonin in a bodily fluid. In such embodiments, a sensor 40 may take the form of a chemical sensor that is sensitive to the level of melatonin or a metabolite of melatonin in the bodily fluid, and estimate the time that patient 12 will attempt to fall asleep based on the detection. For example, processor 46 may compare the melatonin level or rate of change in the melatonin level to a threshold level stored in memory 48, and identify the time that threshold value is exceeded. Processor 46 may identify the time that patient 12 is attempting to fall asleep as the time that the threshold is exceeded, or some amount of time after the threshold is exceeded. Any of a variety of combinations or variations of the above-described techniques may be used to determine when patient 12 is attempting to fall asleep, and a specific one or more techniques may be selected based on the sleeping and activity habits of a particular patient.

Processor 46 may also determine when patient 12 is asleep, e.g., identify the times that patient 12 falls asleep and wakes up, in order to determine one or more sleep quality metric values. The detected values of physiological parameters of patient 12, such as activity level, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response may discernibly change when patient 12 falls asleep or wakes up. In particular, these physiological parameters may be at low values when patient 12 is asleep. Further, the variability of at least some of these parameters, such as heart rate and respiration rate, may be at a low value when the patient is asleep.

Consequently, in order to detect when patient 12 falls asleep and wakes up, processor 46 may monitor one or more of these physiological parameters, or the variability of these physiological parameters, and detect the discernable changes in their values associated with a transition between a sleeping state and an awake state. In some embodiments, processor 46 may determine a mean or median value for a parameter based on values of a signal over time, and determine whether patient 12 is asleep or awake based on the mean or median value. Processor 46 may compare one or more parameter or parameter variability values to thresholds stored in memory 48 to detect when patient 12 falls asleep or awakes. The thresholds may be absolute values of a physiological parameter, or time rate of change values for the physiological parameter, e.g., to detect sudden changes in the value of a parameter or parameter variability. In some embodiments, a threshold used by processor 46 to determine whether patient 12 is asleep may include a time component. For example, a threshold may require that a physiological parameter be above or below a threshold value for a period of time before processor 46 determines that patient is awake or asleep.

In some embodiments, in order to determine whether patient 12 is asleep, processor 46 monitors a plurality of physiological parameters, and determines a value of a metric that indicates the probability that patient 12 is asleep for each of the parameters based on a value of the parameter. In particular, the processor 46 may apply a function or look-up table to the current, mean or median value, and/or the variability of each of a plurality of physiological parameters to determine a sleep probability metric for each of the plurality of physiological parameters. A sleep probability metric value may be a numeric value, and in some embodiments may be a probability value, e.g., a number within the range from 0 to 1, or a percentage value.

Processor 46 may average or otherwise combine the plurality of sleep probability metric values to provide an overall sleep probability metric value. In some embodiments, processor 46 may apply a weighting factor to one or more of the sleep probability metric values prior to combination. Processor 46 may compare the overall sleep probability metric value to one or more threshold values stored in memory 48 to determine when patient 12 falls asleep or awakes. Use of sleep probability metric values to determine when a patient is asleep based on a plurality of monitored physiological parameters is described in greater detail in a commonly-assigned and copending U.S. patent application Ser. No. 10/825,964, by Ken Heruth and Keith Miesel, entitled "DETECTING SLEEP," which was filed on Apr. 15, 2004, and is incorporated herein by reference in its entirety.

To enable processor 46 to determine when patient 12 is asleep or awake, sensors 40 may include, for example, activity sensors as described above. As another example, sensors 40 may include electrodes located on leads or integrated as part of the housing of IMD 14 that generate an electrogram signal as a function of electrical activity of the heart of patient 12, and processor 46 may monitor the heart rate of patient 12 based on the electrogram signal. In other embodiments, a sensor may include an acoustic sensor within IMD 14, a pressure or flow sensor within the bloodstream or cerebrospinal fluid of patient 12, or a temperature sensor located within the bloodstream of patient 12. The signals generated by such sensors may vary as a function of contraction of the heart of patient 12, and can be used by IMD 14 to monitor the heart rate of patient 12.

In some embodiments, sensors 40 may include an electrode pair, including one electrode integrated with the housing of IMD 14 and one of electrodes 42, that generates a signal as a function of the thoracic impedance of patient 12, which varies as a function of respiration by patient 12. In other embodiments, sensors 40 may include a strain gage, bonded piezoelectric element, or pressure sensor within the blood or cerebrospinal fluid that generates a signal that varies based on patient respiration. An electrogram generated by electrodes as discussed above may also be modulated by patient respiration, and may be used as an indirect representation of respiration rate.

Sensors 40 may include electrodes that generate an electromyogram (EMG) signal as a function of muscle electrical activity, or may include any of a variety of known temperature sensors to generate a signal as a function of a core temperature of patient 12. Such electrodes and temperature sensors may be incorporated within the housing of IMD 14, or coupled to IMD 14 via leads. Sensors 40 may also include a pressure sensor within, or in contact with, a blood vessel. The pressure sensor may generate a signal as a function of the a blood pressure of patient 12, and may, for example, comprise a Chronicle Hemodynamic Monitor™ commercially available from Medtronic, Inc. of Minneapolis, Minn.

Sensors 40 may also include optical pulse oximetry sensors or Clark dissolved oxygen sensors located within, as part of a housing of, or outside of IMD 14, which generate signals as a function of blood oxygen saturation and blood oxygen partial pressure respectively. In some embodiments, system 10 may include a catheter with a distal portion located within the cerebrospinal fluid of patient 12, and the distal end may include a Clark dissolved oxygen sensor to generate a signal as a function of the partial pressure of oxygen within the cerebrospinal fluid. Embodiments in which an IMD comprises an implantable pump, for example, may include a catheter with a distal portion located in the cerebrospinal fluid.

In some embodiments, sensors 40 may include one or more intraluminal, extraluminal, or external flow sensors positioned to generate a signal as a function of arterial blood flow. A flow sensor may be, for example, an electromagnetic, thermal convection, ultrasonic-Doppler, or laser-Doppler flow sensor. Further, in some external medical device embodiments of the invention, sensors 40 may include one or more electrodes positioned on the skin of patient 12 to generate a signal as a function of galvanic skin response.

Processor 46 may also detect arousals and/or apneas that occur when patient 12 is asleep based on one or more of the above-identified physiological parameters. For example, processor 46 may detect an arousal based on an increase or sudden increase in one or more of heart rate, heart rate variability, respiration rate, respiration rate variability, blood pressure, or muscular activity as the occurrence of an arousal. Processor 46 may detect an apnea based on a disturbance in the respiration rate of patient 12, e.g., a period with no respiration. Memory 48 may store thresholds used by processor 46 to detect arousals and apneas. Processor 46 may determine, as a sleep quality metric value, the number of apnea events and/or arousals during a night.

Further, in some embodiments, processor 46 may determine which sleep state patient 12 is in during sleep, e.g., REM, S1, S2, S3, or S4, based on one or more of the monitored physiological parameters. In particular, memory 48 may store one or more thresholds for each of sleep states, and processor 46 may compare physiological parameter or sleep probability metric values to the thresholds to determine which sleep state patient 12 is currently in. Processor 46 may determine, as sleep quality metric values, the amounts of time per night spent in the various sleep states. As discussed above, inadequate time spent in deeper sleep states, e.g., S3 and S4, is an indicator of poor sleep quality. Consequently, in some embodiments, processor 46 may determine an amount or percentage of time spent in one or both of the S3 and S4 sleep states as a sleep quality metric.

Figure 3:
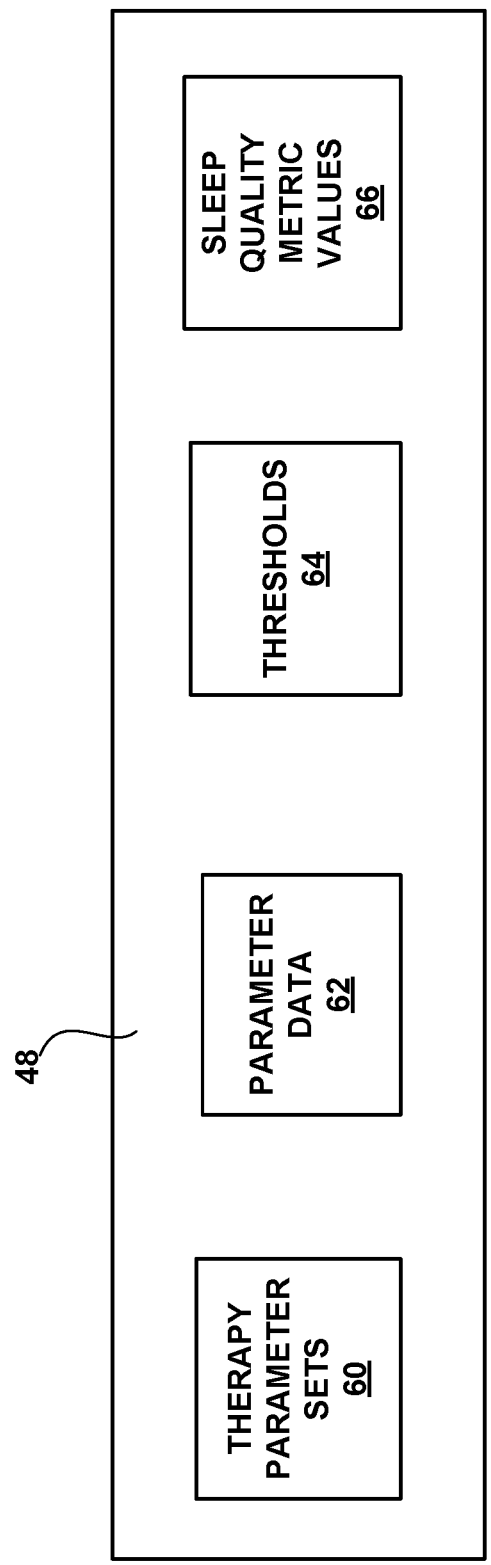
FIG. 3 is a block diagram illustrating an example memory of the implantable medical device of FIG. 1.

FIG. 3 further illustrates memory 48 of IMD 14. As illustrated in FIG. 3, memory 48 stores information describing a plurality of therapy parameter sets 60. Therapy parameter sets 60 may include parameter sets specified by a clinician using clinician programmer 20. Therapy parameter sets 60 may also include parameter sets that are the result of patient 12 changing one or more parameters of one of the preprogrammed therapy parameter sets via patient programmer 26.

Memory 48 may also include parameter information 62 recorded by processor 46, e.g., physiological parameter values, or mean or median physiological parameter values. Memory 48 stores threshold values 64 used by processor 46 in the collection of sleep quality metric values, as discussed above. In some embodiments, memory 48 also stores one or more functions or look-up tables (not shown) used by processor 46 to determine sleep probability metric values, or to determine an overall sleep quality metric value.

Further, processor 46 stores determined values 66 for one or more sleep quality metrics within memory 48. Processor 46 may collect sleep quality metric values 66 each time patient 12 sleeps, or only during selected times that patient 12 is asleep. Processor 46 may store each sleep quality metric value determined within memory 48 as a sleep quality metric value 66, or may store mean or median sleep quality metric values over periods of time such as weeks or months as sleep quality metric values 66. Further, processor 46 may apply a function or look-up table to a plurality of sleep quality metric values to determine overall sleep quality metric value, and may store the overall sleep quality metric values within memory 48. The application of a function or look-up table by processor 46 for this purpose may involve the use or weighting factors for one or more of the individual sleep quality metric values.

In some embodiments, processor 46 identifies which of therapy parameter sets 60 is currently selected for use in delivering therapy to patient 12 when a value of one or more sleep quality metrics is collected, and may associate that value with the current therapy parameter set. For example, for each of the plurality of therapy parameter sets 60, processor 46 may store a representative value of each of one or more sleep quality metrics within memory 48 as a sleep quality metric value 66 with an indication of which of the therapy parameter sets that representative value is associated with. A representative value of sleep quality metric for a therapy parameter set may be the mean or median of collected sleep quality metric values that have been associated with that therapy parameter set.

As shown in FIG. 2, IMD 14 also includes a telemetry circuit 50 that allows processor 46 to communicate with clinician programmer 20 and patient programmer 26. Processor 46 may receive information identifying therapy parameter sets 60 preprogrammed by the clinician and threshold values 64 from clinician programmer 20 via telemetry circuit 50 for storage in memory 48. Processor 46 may receive an indication of the therapy parameter set 60 selected by patient 12 for delivery of therapy, or adjustments to one or more of therapy parameter sets 60 made by patient 12, from patient programmer 26 via telemetry circuit 50. Programmers 20, 26 may receive sleep quality metric values 66 from processor 46 via telemetry circuit 50.

Figure 4:
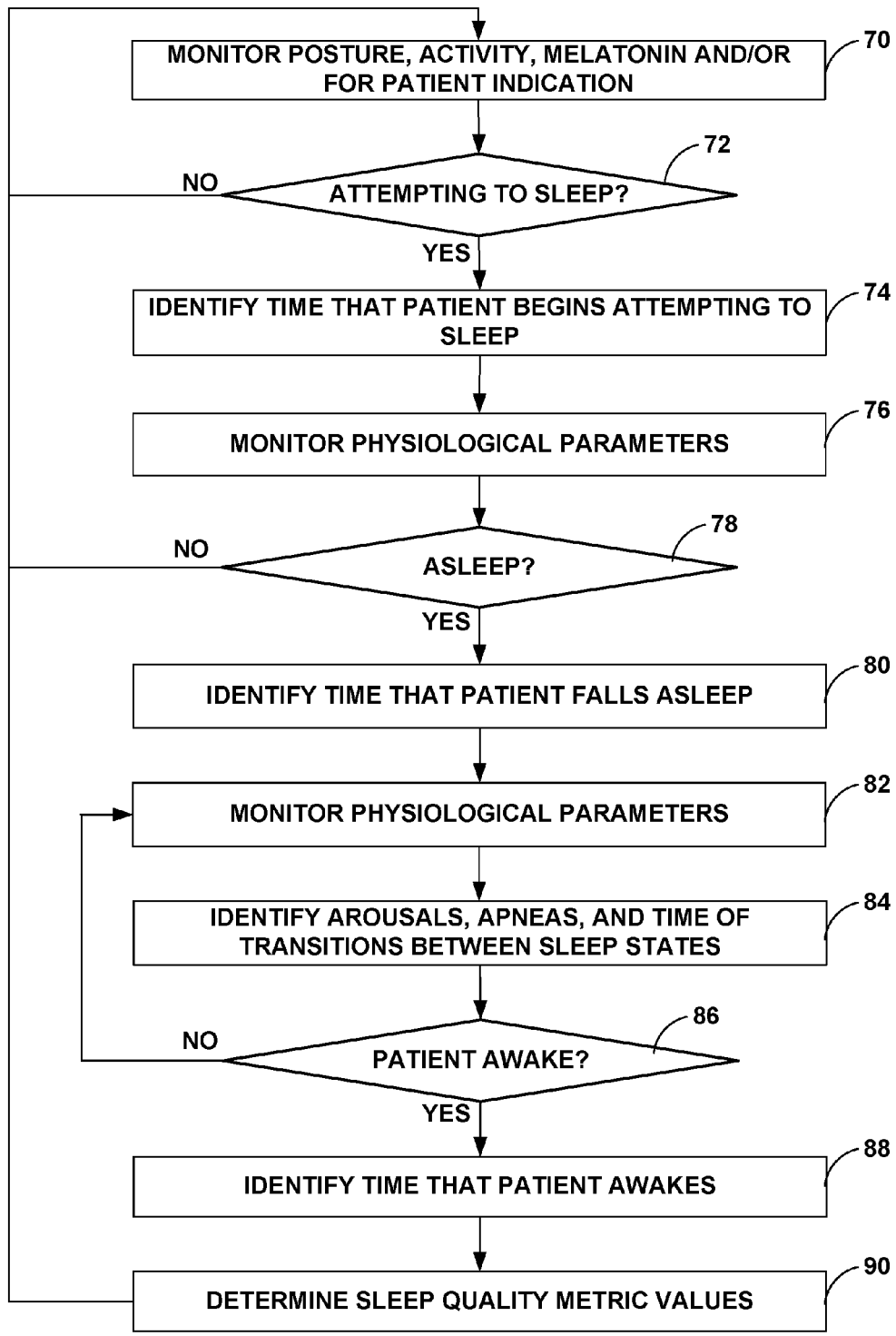
FIG. 4 is a flow diagram illustrating an example method for collecting sleep quality information that may be employed by an implantable medical device.

FIG. 4 is a flow diagram illustrating an example method for collecting sleep quality information that may be employed by IMD 14. IMD 14 monitors the posture, activity level, and/or melatonin level of patient 12, or monitors for an indication from patient 12, e.g., via patient programmer 26 (70), and determines whether patient 12 is attempting to fall asleep based on the posture, activity level, melatonin level, and/or a patient indication, as described above (72). If IMD 14 determines that patient 12 is attempting to fall asleep, IMD 14 identifies the time that patient 12 began attempting to fall asleep using any of the techniques described above (74), and monitors one or more of the various physiological parameters of patient 12 discussed above to determine whether patient 12 is asleep (76, 78).

In some embodiments, IMD 14 compares parameter values or parameter variability values to one or more threshold values 64 to determine whether patient 12 is asleep. In other embodiments, IMD 14 applies one or more functions or look-up tables to determine one or more sleep probability metric values based on the physiological parameter values, and compares the sleep probability metric values to one or more threshold values 64 to determine whether patient 12 is asleep. While monitoring physiological parameters (76) to determine whether patient 12 is asleep (78), IMD 14 may continue to monitor the posture and/or activity level of patient 12 (70) to confirm that patient 12 is still attempting to fall asleep (72).

When IMD 14 determines that patient 12 is asleep, e.g., by analysis of the various parameters contemplated herein, IMD 14 will identify the time that patient 12 fell asleep (80). While patient 12 is sleeping, IMD 14 will continue to monitor physiological parameters of patient 12 (82). As discussed above, IMD 14 may identify the occurrence of arousals and/or apneas based on the monitored physiological parameters (84). Further, IMD 14 may identify the time that transitions between sleep states, e.g., REM, S1, S2, S3, and S4, occur based on the monitored physiological parameters (84).

Additionally, while patient 12 is sleeping, IMD 14 monitors physiological parameters of patient 12 (82) to determine whether patient 12 has woken up (86). When IMD 14 determines that patient 12 is awake, IMD 14 identifies the time that patient 12 awoke (88), and determines sleep quality metric values based on the information collected while patient 12 was asleep (90).

For example, one sleep quality metric value IMD 14 may calculate is sleep efficiency, which IMD 14 may calculate as a percentage of time during which patient 12 is attempting to sleep that patient 12 is actually asleep. IMD 14 may determine a first amount of time between the time IMD 14 identified that patient 12 fell asleep and the time IMD 14 identified that patient 12 awoke. IMD 14 may also determine a second amount of time between the time IMD 14 identified that patient 12 began attempting to fall asleep and the time IMD 14 identified that patient 12 awoke. To calculate the sleep efficiency, IMD 14 may divide the first time by the second time.

Another sleep quality metric value that IMD 14 may calculate is sleep latency, which IMD 14 may calculate as the amount of time between the time IMD 14 identified that patient 12 was attempting to fall asleep and the time IMD 14 identified that patient 12 fell asleep. Other sleep quality metrics with values determined by IMD 14 based on the information collected by IMD 14 in the illustrated example include: total time sleeping per day, at night, and during daytime hours; number of apnea and arousal events per occurrence of sleep; and amount of time spent in the various sleep states, e.g., one or both of the S3 and S4 sleep states. IMD 14 may store the determined values as sleep quality metric values 66 within memory 48.

IMD 14 may perform the example method illustrated in FIG. 4 continuously, e.g., may monitor to identify when patient 12 is attempting to sleep and asleep any time of day, each day. In other embodiments, IMD 14 may only perform the method during evening hours and/or once every N days to conserve battery and memory resources. Further, in some embodiments, IMD 14 may only perform the method in response to receiving a command from patient 12 or a clinician via one of programmers 20, 26. For example, patient 12 may direct IMD 14 to collect sleep quality information at times when the patient believes that his or her sleep quality is low or therapy is ineffective.

Figure 5:
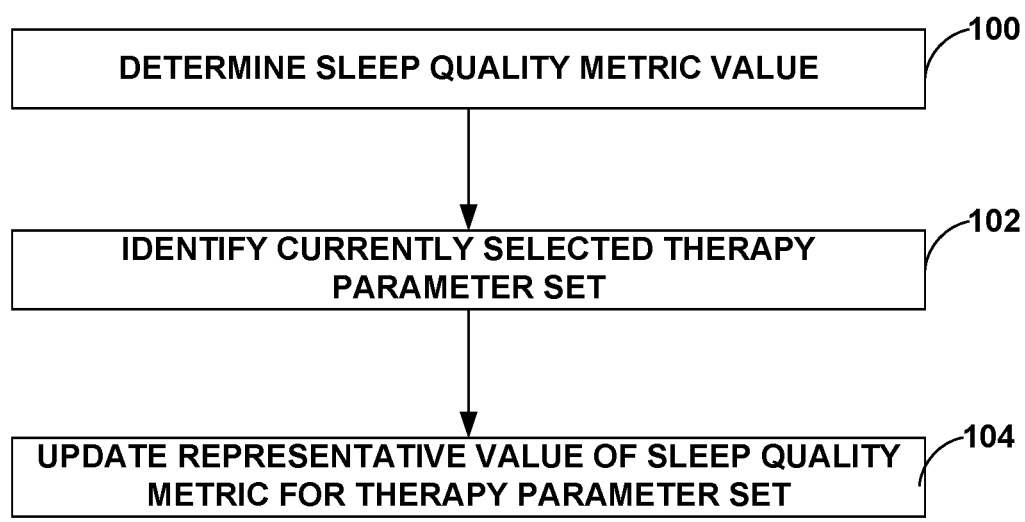
FIG. 5 is a flow diagram illustrating an example method for associating sleep quality information with therapy parameter sets that may be employed by an implantable medical device.

FIG. 5 is a flow diagram illustrating an example method for associating sleep quality information with therapy parameter sets 60 that may be employed by IMD 14. IMD 14 determines a value of a sleep quality metric according to any of the techniques described above (100). IMD 14 also identifies the current therapy parameter set, e.g., the therapy parameter set 60 used by IMD 14 to control delivery of therapy when patient 12 was asleep (102), and associates the newly determined value with the current therapy parameter set 60.

Among sleep quality metric values 66 within memory 48, IMD 14 stores a representative value of the sleep quality metric, e.g., a mean or median value, for each of the plurality of therapy parameter sets 60. IMD 14 updates the representative values for the current therapy parameter set based on the newly determined value of the sleep quality metric. For example, a newly determined sleep efficiency value may be used to determine a new average sleep efficiency value for the current therapy parameter set 60.

Figure 6:
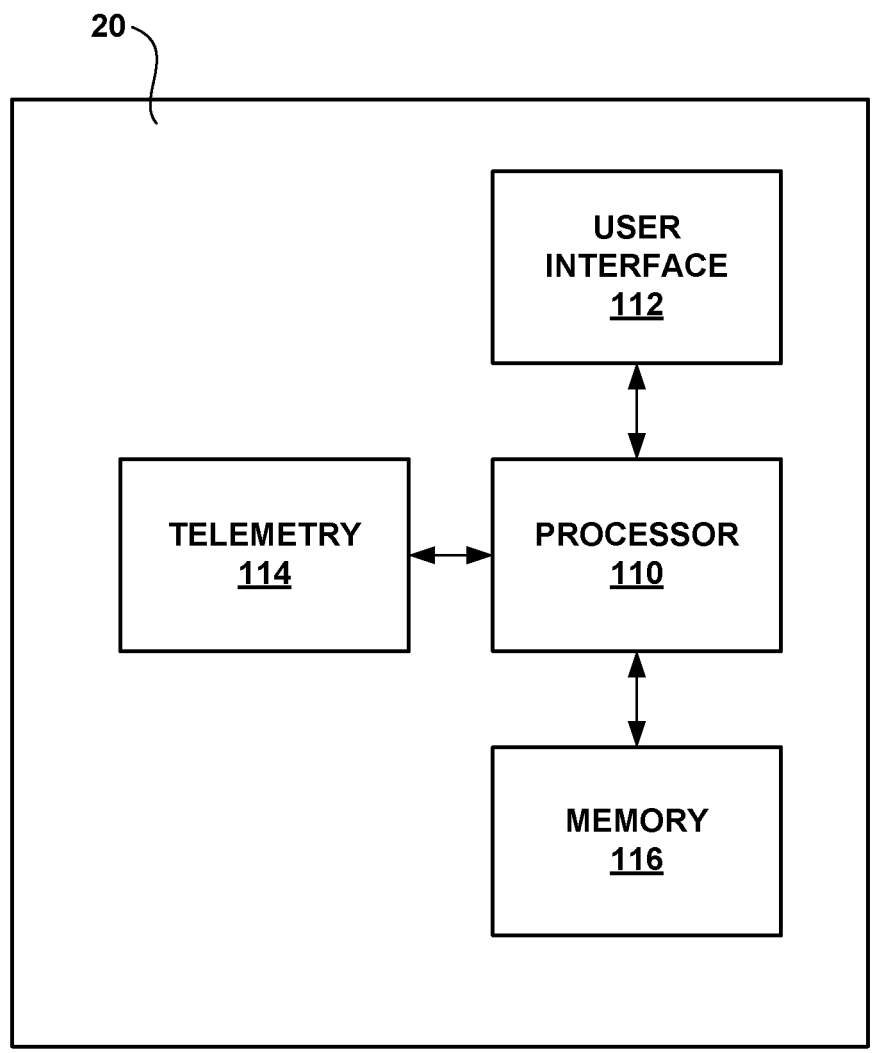
FIG. 6 is a block diagram illustrating an example clinician programmer.

FIG. 6 is a block diagram further illustrating clinician programmer 20. A clinician may interact with a processor 110 via a user interface 112 in order to program therapy for patient 12. Further, processor 110 may receive sleep quality metric values 66 from IMD 14 via a telemetry circuit 114, and may generate sleep quality information for presentation to the clinician via user interface 112. User interface 112 may include display 22 and keypad 24, and may also include a touch screen or peripheral pointing devices as described above. Processor 110 may include a microprocessor, a controller, a DSP, an ASIC, an FPGA, discrete logic circuitry, or the like.

Clinician programmer 20 also includes a memory 116. Memory 116 may include program instructions that, when executed by processor 110, cause clinician programmer 20 to perform the functions ascribed to clinician programmer 20 herein. Memory 116 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 7:
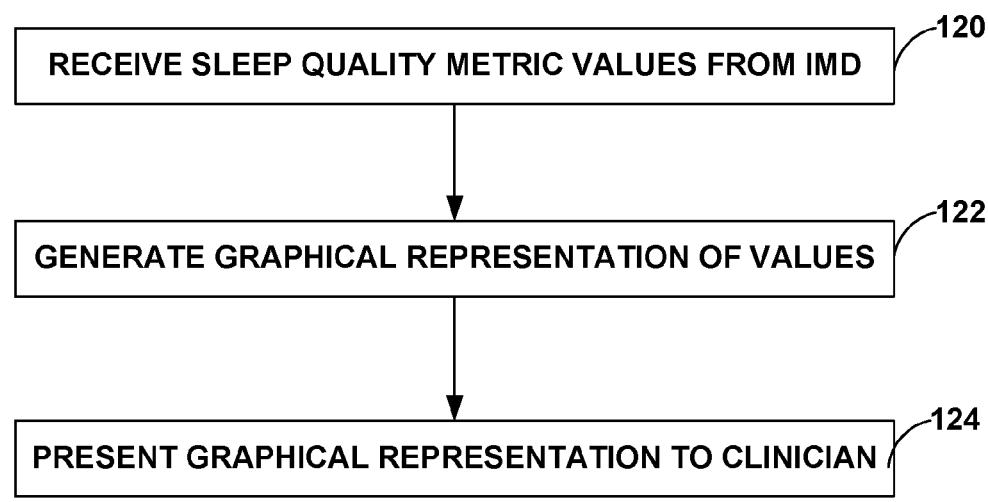
FIG. 7 is a flow diagram illustrating an example method for presenting sleep quality information to a clinician that may be employed by a clinician programmer.

FIG. 7 is a flow diagram illustrating an example method for presenting sleep quality information to a clinician that may be employed by clinician programmer 20. Clinician programmer 20 receives sleep quality metric values 66 from IMD 14, e.g., via telemetry circuit 114 (120). The sleep quality metric values 66 may be daily values, or mean or median values determined over greater periods of time, e.g., weeks or months.

Clinician programmer 20 may simply present the values to the clinician via display 22 in any form, such as a table of average values, or clinician programmer 20 may generate a graphical representation of the sleep quality metric values (122). For example, clinician programmer 20 may generate a trend diagram illustrating sleep quality metric values 66 over time, or a histogram, pie chart, or other graphic illustration of percentages of sleep quality metric values 66 collected by IMD 14 that were within ranges. Where clinician programmer 20 generates a graphical representation of the sleep quality metric values 66, clinician programmer 20 presents the graphical representation to the clinician via display 22 (124).

Figure 8:
FIG. 8 illustrates an example list of therapy parameter sets and associated sleep quality information that may be presented by a clinician programmer.

FIG. 8 illustrates an example list 130 of therapy parameter sets and associated sleep quality metric values that may be presented to a clinician by clinician programmer 20. Each row of example list 130 includes an identification of one of therapy parameter sets 60, the parameters of the set, and a representative value for one or more sleep quality metrics associated with the identified therapy parameter set, such as sleep efficiency, sleep latency, or both. The example list 130 includes representative values for sleep efficiency, sleep latency, and "deep sleep," e.g., the average amount of time per night spent in either of the S3 and S4 sleep states.

Figure 9:
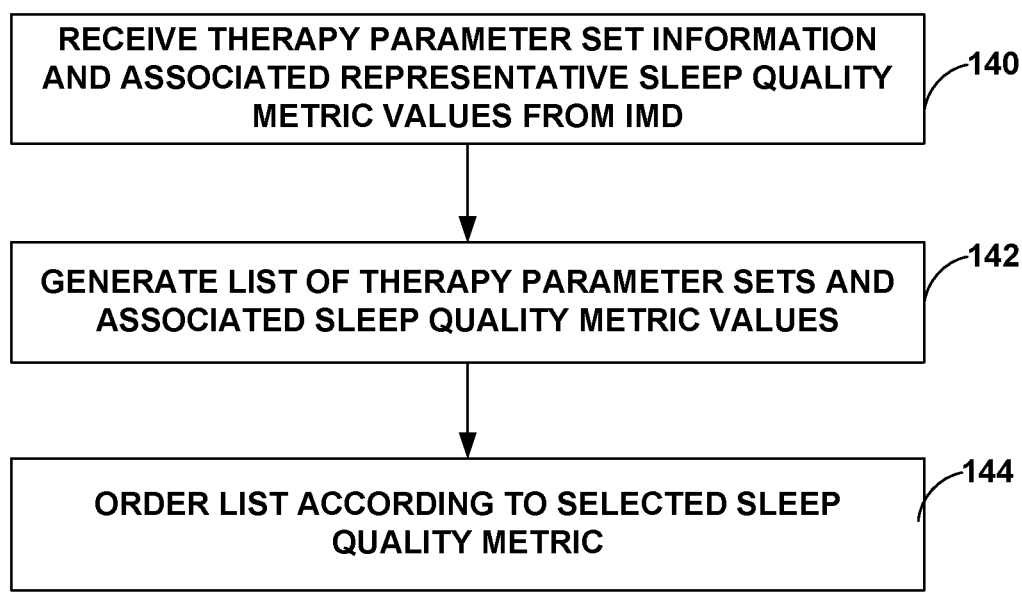
FIG. 9 is a flow diagram illustrating an example method for displaying a list of therapy parameter sets and associated sleep quality information that may be employed by a clinician programmer.

FIG. 9 is a flow diagram illustrating an example method for displaying a list 130 of therapy parameter sets and associated sleep quality information that may be employed by clinician programmer 20. According to the example method, clinician programmer 20 receives information identifying the plurality of therapy parameter sets 60 stored in memory 48 of IMD 14, and one or more representative sleep quality metric values associated with each of the therapy parameter sets (140). Clinician programmer 20 generates a list 130 of the therapy parameter sets 60 and any associated representative sleep quality metric values (142), and orders the list according to a selected sleep quality metric (144). For example, in the example list 130 illustrated in FIG. 8, the clinician may select whether list 130 should be ordered according to sleep efficiency or sleep latency via user interface 112 of clinician programmer 20.

Figure 10:
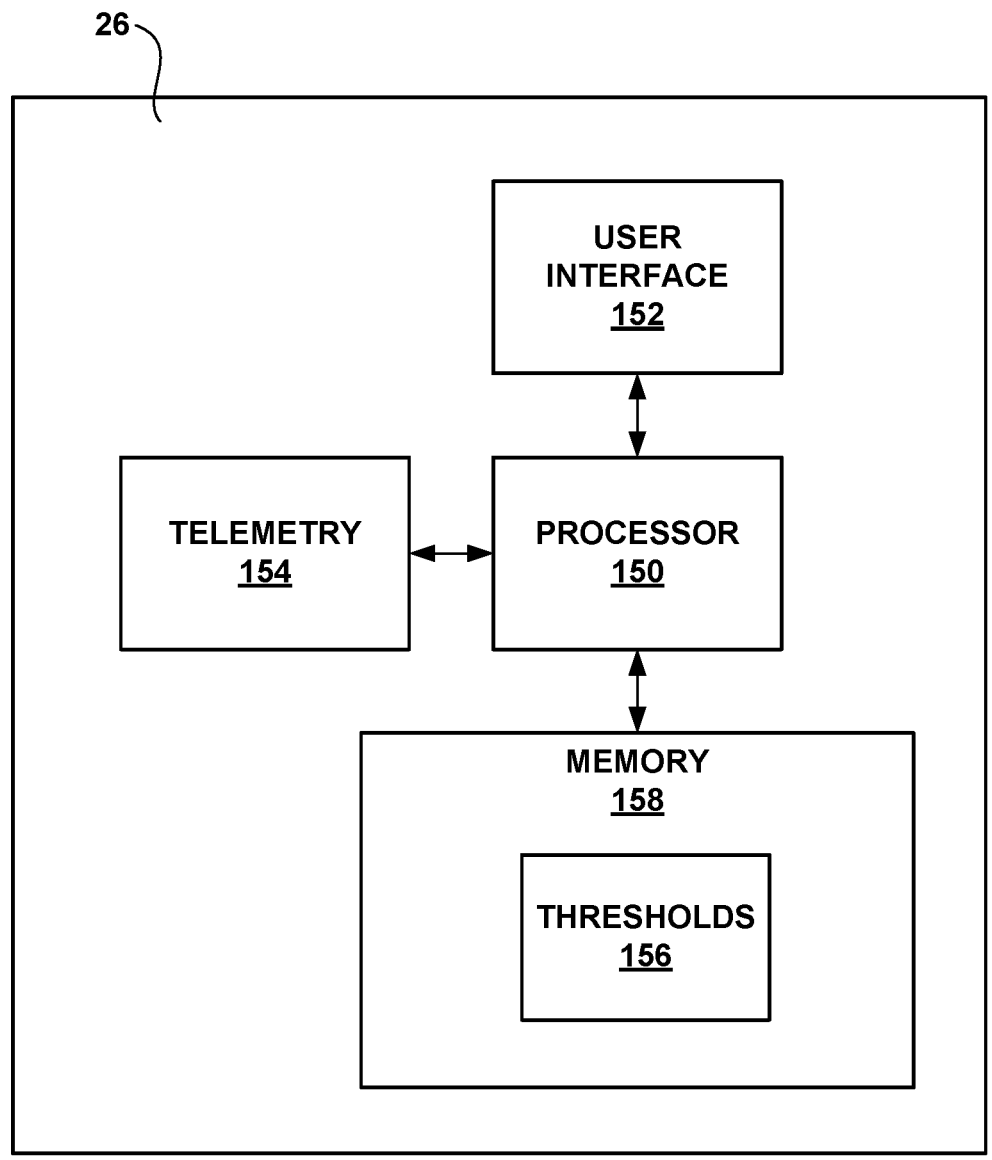
FIG. 10 is a block diagram illustrating an example patient programmer.

FIG. 10 is a block diagram further illustrating patient programmer 26. Patient 12 may interact with a processor 150 via a user interface 152 in order to control delivery of therapy, i.e., select or adjust one or more of therapy parameter sets 60 stored by IMD 14. Processor 150 may also receive sleep quality metric values 66 from IMD 14 via a telemetry circuit 154, and may provide messages related to sleep quality to patient 12 via user interface 152 based on the received values. User interface 152 may include display 28 and keypad 30, and may also include a touch screen or peripheral pointing devices as described above.

In some embodiments, processor 150 may determine whether to provide a message related to sleep quality to patient 12 based on the received sleep quality metric values. For example, processor 150 may periodically receive sleep quality metric values 66 from IMD 14 when placed in telecommunicative communication with IMD 14 by patient 12, e.g., for therapy selection or adjustment. Processor 150 may compare these values to one or more thresholds 156 stored in a memory 158 to determine whether the quality of the patient's sleep is poor enough to warrant a message.

Processor 150 may present messages to patient 12 as text via display, and/or as audio via speakers included as part of user interface 152. The message may, for example, direct patient 12 to see a physician, increase therapy intensity before sleeping, or select a different therapy parameter set before sleeping than the patient had typically selected previously. In some embodiments, the message may indicate the quality of sleep to patient 12 to, for example, provide patient 12 with an objective indication of whether his or her sleep quality is good, adequate, or poor. Further, in some embodiments processor 150 may, like clinician programmer 20, receive representative sleep quality metric values. In such embodiments, processor 150 may identify a particular one or more of therapy parameter sets 60 to recommend to patient 12 based on representative sleep quality metric values associated with those programs.

Processor 150 may include a microprocessor, a controller, a DSP, an ASIC, an FPGA, discrete logic circuitry, or the like. Memory 158 may also include program instructions that, when executed by processor 150, cause patient programmer 26 to perform the functions ascribed to patient programmer 26 herein. Memory 158 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 11:
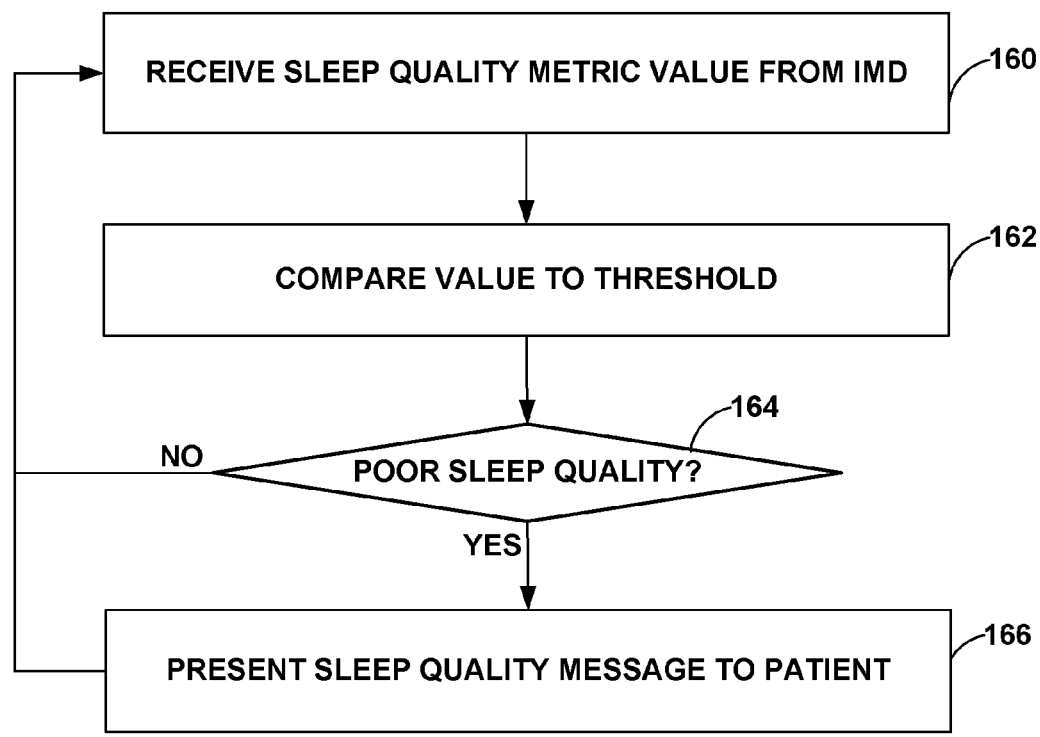
FIG. 11 is a flow diagram illustrating an example method for presenting a sleep quality message to a patient that may be employed by a patient programmer.

FIG. 11 is a flow diagram illustrating an example method for presenting a sleep quality message to patient 12 that may be employed by patient programmer 26. According to the illustrated example method, patient programmer 26 receives a sleep quality metric value from IMD 14 (160), and compares the value to a threshold value 156 (162). Patient programmer 26 determines whether the comparison indicates poor sleep quality (164). If the comparison indicates that the quality of sleep experienced by patient 12 is poor, patient programmer 26 presents a message related to sleep quality to patient 12 (166).

Various embodiments of the invention have been described. However, one skilled in the art will recognize that various modifications may be made to the described embodiments without departing from the scope of the invention. For example, although described herein primarily in the context of treatment of pain with an implantable neurostimulator, the invention is not so limited. The invention may be embodied in any implantable medical device, such as a cardiac pacemaker, an implantable pump, or an implantable monitor that does not itself deliver a therapy to the patient. Further, the invention may be implemented via an external, e.g., non-implantable, medical device. In such embodiments, the external medical device itself may include a user interface and display to present sleep information to a user, such as a clinician or patient, based on determined sleep quality metric values.

As another example, the invention may be embodied in a trial neurostimulator, which is coupled to percutaneous leads implanted within the patient to determine whether the patient is a candidate for neurostimulation, and to evaluate prospective neurostimulation therapy parameter sets. Similarly, the invention may be embodied in a trial drug pump, which is coupled to a percutaneous catheter implanted within the patient to determine whether the patient is a candidate for an implantable pump, and to evaluate prospective therapeutic agent delivery parameter sets. Sleep quality metric values collected by the trial neurostimulator or pump may be used by a clinician to evaluate the prospective therapy parameter sets, and select parameter sets for use by the later implanted non-trial neurostimulator or pump. In particular, a trial neurostimulator or pump may determine representative values of one or more sleep quality metrics for each of a plurality of prospective therapy parameter sets, and a clinician programmer may present a list of prospective parameter sets and associated representative values to a clinician. The clinician may use the list to identify potentially efficacious parameter sets, and may program a permanent implantable neurostimulator or pump for the patient with the identified parameter sets.

Further, the invention is not limited to embodiments in which an implantable or external medical device determines sleep quality metric values. Instead a medical device according to the invention may record values for one or more physiological parameters, and provide the physiological parameter values to a programming device, such as programmers 20, 26. In such embodiments, the programming device, and more particularly a processor of the programming device, e.g., processors 110, 150, employs any of the techniques described herein with reference to IMD 14 in order to determine sleep quality metric values based on the physiological parameter values received from the medical device. The programming device may receive physiological parameter values from the medical device in real time, or may monitor physiological parameters of the patient by receiving and analyzing physiological parameter values recorded by the medical device over a period of time. In some embodiments, in addition to physiological parameter values, the medical device provides the programming device information identifying times at which the patient indicated that he or she was attempting to fall asleep, which the programming device may use to determine one or more sleep quality metric values as described herein.

In some embodiments, the medical device may associate recorded physiological parameter values with current therapy parameter sets. The medical device may provide information indicating the associations of recorded physiological parameter values and therapy parameter sets to the programming device. The programming device may determine sleep quality metric values and representative sleep quality metric values for each of the plurality of therapy parameter sets based on the physiological parameter values associated with the therapy parameter sets, as described herein with reference to IMD 14.

The invention may also be embodied as a computer-readable medium that includes instructions to cause a processor to perform any of the methods described herein. These and other embodiments are within the scope of the following claims.

What is claimed is:

1. A method comprising:
   delivering, by a medical device system, electrical stimulation therapy to a patient according to a plurality of different therapy parameter sets;
   monitoring, by the medical device system, at least one physiological parameter of the patient;
   determining when the patient is asleep, and detecting occurrences of at least one of arousals and apneas when the patient is asleep based on the at least one physiological parameter;
   associating each detected occurrence of an arousal or an apnea with a corresponding one of the plurality of different therapy parameter sets according to which the medical device delivered the therapy when the occurrence of the arousal or the apnea was detected;
   for each of the plurality of different therapy parameter sets:
      determining a plurality of values of a sleep quality metric based on the occurrences of the at least one of arousals and apneas associated with the corresponding therapy parameter set, each value of the plurality of values of the sleep quality metric indicating a number of the arousals or apneas over a period of time; and
      determining a representative value of the sleep quality metric for the therapy parameter set based on the plurality of values of the sleep quality metric associated with the therapy parameter set;
   storing the representative values of the sleep quality metric and an indication of the association of the therapy parameter sets with the respective representative values of the sleep quality metric; and
   automatically adjusting the delivery of the electrical stimulation therapy to the patient based on the determined representative values.

2. The method of claim 1, wherein monitoring at least one physiological parameter comprises monitoring at least one of activity level, posture, respiration rate, respiratory volume, blood oxygen saturation, partial pressure of oxygen within blood, muscular activity, or arterial blood flow.

3. The method of claim 1, wherein monitoring at least one physiological parameter comprises monitoring at least one of heart rate or blood pressure.

4. The method of claim 1, further comprising presenting sleep quality information to a user based on the plurality of values of the sleep quality metric.

5. The method of claim 4, wherein presenting sleep quality information to the user comprises presenting a graphical representation of the sleep quality metric values.

6. The method of claim 5, wherein presenting the graphical representation comprises presenting at least one of a trend diagram, a histogram and a pie chart based on the plurality of values of the sleep quality metric.

7. The method of claim 4, wherein presenting sleep quality information to the user comprises presenting a message related to sleep quality to the patient via a patient programmer.

8. The method of claim 1, wherein detecting the occurrences of at least one of arousals and apneas when the patient is asleep based on the at least one physiological parameter comprises detecting the occurrences of at least one of arousals and apneas based on sudden changes in at least one of heart rate, respiration rate, or blood pressure.

9. The method of claim 1, wherein detecting the occurrences of at least one of arousals and apneas when the patient is asleep based on the at least one physiological parameter comprises detecting the occurrences of at least one of arousals and apneas based on sudden changes in a variability of the at least physiological parameter.

10. The method of claim 1, wherein delivering therapy to the patient comprises delivering neurostimulation therapy to the patient.

11. The method of claim 1, wherein delivering therapy to the patient comprises delivering cardiac pacing therapy to the patient.

12. The method of claim 1, further comprising:
   presenting a list of the therapy parameter sets and associated representative values to a user; and
   ordering the list of therapy parameter sets according to the associated representative values.

13. A medical system comprising:
   a medical device configured to deliver an electrical stimulation therapy to a patient via a plurality of electrodes according to a plurality of different therapy parameter sets;
   a monitor configured to monitor at least one physiological parameter of the patient;
   a processor configured to determine when the patient is asleep, and detect occurrences of at least one of arousals or apneas when the patient is asleep based on the at least one physiological parameter,
   wherein the processor is configured to associate each detected occurrence of an arousal or an apnea with a corresponding one of the plurality of therapy parameter sets according to which the medical device delivered the therapy when the occurrence of the arousal or the apnea was detected, wherein, for each of the plurality of therapy parameter sets, the processor is configured to:
  determine a plurality of values of a sleep quality metric based on the occurrences of the at least one of arousals or apneas associated with the corresponding therapy parameter set, each value of the plurality of values of the sleep quality metric indicating a number of the arousals or apneas over a period of time, and
  determine a representative value of the sleep quality metric for the therapy parameter set based on the plurality of values of the sleep quality metric associated with the therapy parameter set; and
a memory that stores the representative values of the sleep quality metric and an indication of the association of the therapy parameter sets with the respective representative values of the sleep quality metric,
wherein the medical device is configured to automatically adjust the delivery of the electrical stimulation therapy to the patient based on the determined representative values.

14. The medical system of claim 13, wherein the at least one physiological parameter comprises at least one of activity level, posture, respiration rate, respiratory volume, blood oxygen saturation, partial pressure of oxygen within blood, muscular activity, or arterial blood flow.

15. The medical system of claim 13, wherein the at least one physiological parameter comprises at least one of heart rate or blood pressure.

16. The medical system of claim 13, further comprising one or more computing devices separate from the medical device, wherein the one or more computing devices comprise the processor, wherein at least one of the one or more computing devices presents sleep quality information to a user based on the values of the sleep quality metric determined by the processor.

17. The medical system of claim 16, wherein the user comprises a clinician, and the computing device comprises a clinician programmer that presents at least one of a trend diagram, a histogram or a pie chart to the clinician based on the values of the sleep quality metric.

18. The medical system of claim 16, wherein the user comprises a patient, and the computing device comprises a patient programmer that presents a message related to sleep quality to the patient based on the values of the sleep quality metric.

19. The medical system of claim 13,
  further comprising one or more computing devices separate from the medical device, wherein the one or more computing devices comprise the processor,
  wherein at least one of the one or more computing devices presents a list of the therapy parameter sets and the associated representative values to a user, and orders the list of therapy parameter sets according to the associated representative values.

20. The medical system of claim 13, wherein the medical device comprises the monitor.

21. The medical system of claim 13, wherein the medical device comprises the processor.

22. The medical system of claim 13, wherein the representative value for each therapy parameter set comprises one of a mean value or a median value of the numbers of arousals or apneas over the periods of time.

23. The medical system of claim 13, wherein, for each of the plurality of therapy parameter sets, the processor determines the value of the overall sleep quality metric by applying a function or look-up table to the determined values of each of the plurality of sleep quality metrics associated with that particular therapy parameter set.

24. The medical system of claim 13, wherein the processor is configured to detect the at least one of arousals and apneas based on sudden changes in occurrences of at least one of heart rate, respiration rate, or blood pressure.

25. The medical system of claim 13, wherein the processor is configured to detect the occurrences of at least one of arousals and apneas based on sudden changes in a variability of the at least physiological parameter.

26. The medical system of claim 13, wherein the medical device comprises an implantable medical device.

27. The medical system of claim 13, wherein the medical device is configured to deliver neurostimulation therapy to the patient.

28. The medical system of claim 13, wherein the medical device comprises a cardiac rhythm management device configured to deliver a cardiac pacing therapy to the patient.

29. A medical system comprising:
  an implantable medical device comprising:
    therapy delivery circuitry configured to deliver an electrical stimulation therapy to a patient via a plurality of electrodes according to a plurality of different therapy parameter sets;
    sensing circuitry configured to sense at least one physiological parameter of the patient;
  a processor configured to:
    determine when the patient is asleep;
    detect occurrences of at least one of arousals or apneas when the patient is asleep based on a variability of the at least one physiological parameter; and
    associate each detected occurrence of an arousal or an apnea with a corresponding one of the plurality of therapy parameter sets according to which the medical device delivered the therapy when the occurrence of the arousal or the apnea was detected,
  wherein, for each of the plurality of therapy parameter sets, the processor is configured to:
    determine a plurality of values of a sleep quality metric based on the occurrences of the at least one of arousals or apneas associated with the therapy parameter set, each value of the plurality of values of the sleep quality metric indicating a number of the arousals or apneas over a period of time, and
    determine a representative value of the sleep quality metric for the therapy parameter set based on the plurality of values of the sleep quality metric associated with the therapy parameter set; and
  a memory that stores the representative values of the sleep quality metric and an indication of the association of the therapy parameter sets with the respective representative values of the sleep quality metric,
  wherein the processor is configured to automatically adjust the delivery of the electrical stimulation therapy to the patient based on the determined representative values.

* * * * *